United States Patent [19]

Grandjean

[11] Patent Number: 5,358,519
[45] Date of Patent: * Oct. 25, 1994

[54] MUSCLE CONTROL AND MONITORING SYSTEM

[75] Inventor: Pierre A. Grandjean, Bassenge, Belgium

[73] Assignee: Medtronic, Inc., Minneapolis, Minn.

[*] Notice: The portion of the term of this patent subsequent to Nov. 26, 2008 has been disclaimed.

[21] Appl. No.: 92,180

[22] Filed: Jul. 15, 1993

Related U.S. Application Data

[63] Continuation-in-part of Ser. No. 786,133, Oct. 31, 1991, abandoned, which is a continuation-in-part of Ser. No. 446,593, Dec. 6, 1989, Pat. No. 5,067,960, Ser. No. 446,592, Dec. 6, 1989, Pat. No. 5,089,019, and Ser. No. 446,811, Dec. 6, 1989, Pat. No. 5,098,442.

[51] Int. Cl.$^5$ ............................................. A61M 1/10
[52] U.S. Cl. .................................... 623/3; 600/16
[58] Field of Search ........................ 623/3; 600/16-18

[56] References Cited

U.S. PATENT DOCUMENTS

| | | | |
|---|---|---|---|
| 4,411,268 | 10/1983 | Cox | 128/421 |
| 4,813,952 | 3/1989 | Khalafalla | 623/3 |
| 5,009,229 | 4/1991 | Grandjean | 128/419 |
| 5,067,960 | 11/1991 | Grandjean | 623/3 |
| 5,089,019 | 2/1992 | Grandjean | 623/3 |
| 5,098,442 | 3/1992 | Grandjean | 623/3 |

*Primary Examiner*—Randy C. Shay
*Attorney, Agent, or Firm*—Gregory P. Gadson; Harold R. Patton

[57] ABSTRACT

Apparatus and method for monitoring the performance of skeletal muscle used in a skeletal muscle powered cardiac assist system. The longest term monitoring is performed by an oxygen sensor which determines the adequacy of circulatory support to the skeletal muscle. An adequately supported skeletal muscle can offer the desired cardiac assistance chronically. Insufficient support indicates that the skeletal muscle will easily fatigue if adequate vascularization is not achieved. If the circulatory support is chronically insufficient, the risk of ischemia becomes high and additional surgical intervention may be required. A somewhat shorter term concern is the adequacy of the conditioning needed to render a fast twitch skeletal muscle useful in assisting the slow twitch myocardium. A pressure transducer is used to measure conditioning sufficiency. A third type of monitoring provides an indication of changes in cardiac requirements utilizing an activity sensor. This indication of cardiac requirements may be used to vary skeletal muscle loading by adjusting duty cycle. The shortest term monitoring and control technique uses a temperature sensor to monitor efficiency skeletal muscle cardiac assist. Efficiency may be improved by adjusting the phase relationship between cardiac contraction and skeletal muscle stimulation.

8 Claims, 20 Drawing Sheets

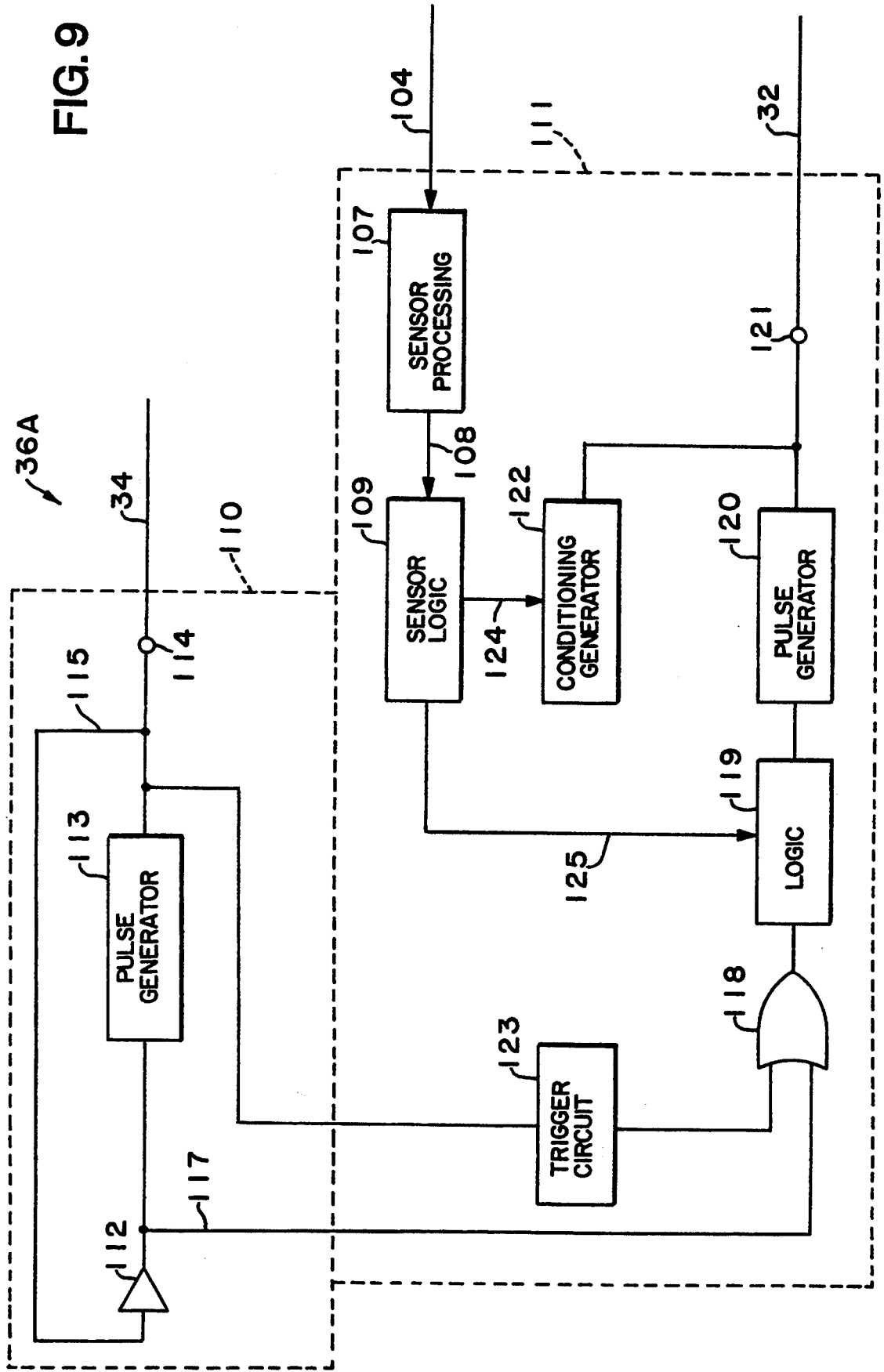

MUSCLE CONTROL AND MONITORING SYSTEM

CROSS REFERENCES TO CO-PENDING APPLICATIONS

This application is a continuation-in-part of commonly assigned U.S. patent application Ser. No. 07/786,133, filed Oct. 31, 1991 entitled "Muscle Control And Monitoring System," now abandoned, and a continuation-in-part of the following commonly assigned U.S. patent Ser. Nos. 446,593, filed Dec. 6, 1989 now U.S. Pat. No. 5,067,960, issued Nov. 26, 1991 for "Muscle Fitness Detection by Colorimetry"; Ser. No. 446,592, filed Dec. 6, 1989, now U.S. Pat. No. 5,089,019, issued Feb. 18, 1992 for "Muscle Output Monitor by Intramuscular Temperature Variation Measurement"; and Ser. No. 446,811, filed Dec. 6, 1989, now U.S. Pat. No. 5,098,442, issued Mar. 24, 1992 for "Muscle Contraction Control by Intramuscular Pressure Monitoring". This application is also related to U.S. Pat. No. 5,009,229, issued Apr. 23, 1991 for "Muscle Stimulator with Variable Duty Cycle".

BACKGROUND OF THE INVENTION

1. Field of the Invention

The present invention relates generally to cardiac assist systems and more particularly, relates to control and monitoring of cardiac assist systems which are powered by skeletal muscle.

2. Description of the Prior Art

Cardiac assist systems do not replace the human heart, but merely supplement it. Many techniques have been proposed using a variety of mechanical power sources. Typically these required some form of percutaneous energy transfer because of the difficulty in storing sufficient energy subcutaneously. Such systems are cumbersome and inconvenient for the patient, and are prone to infection along the percutaneous energy transfer path.

A technique holding a great deal of promise is to power the cardiac assist system from a surgically modified skeletal muscle. The cardiac assist system is thus powered by normal biochemical processes. U.S. Pat. No. 4,813,952 issued to Khalafalla teaches a number of configurations of a skeletal muscle powered cardiac assist system.

One problem peculiar to a skeletal muscle powered cardiac assist system is that the skeletal muscle must be conditioned to with stand the constant load of continuous contraction/relaxation demanded of the myocardium. U.S. Pat. No. 4,411,268 issued to Cox teaches a technique for conditioning the skeletal muscle. Whereas the apparatus of Cox is effective to accomplish this conditioning, his system has no provisions for feedback to permit the self-regulation of the conditioning regimen or for chronically monitoring the stability of the skeletal muscle following the conditioning process. In practice this necessitates the attention of highly skilled medical personnel to monitor the operation of the skeletal muscle with sophisticated instrumentation and to exercise manual control of the stimulation parameters with pulse generator programming equipment. Furthermore, neither Cox nor Khalafalla teach a real time monitoring mechanism, whereby adequate vascular support to the skeletal muscle and accurate stimulation timing can be chronically verified.

A second problem is basic monitoring of the skeletal muscle contractions. This is important because it provides a way to check and modify various pulse generator timing and amplitude parameters. Currently, the prior art suggests no effective means for performing this monitoring function.

Whereas the feasibility of a skeletal muscle powered cardiac assist system has been established in the literature and the clinic, a practical system must address concerns regarding efficiency and safety of operation. Of specific concern is the tying of the rate of stimulation of the skeletal muscle directly to the heart rate. This seems appropriate in some instances, but care must be exercised because of the wide range of possible rates. For example, it may be quite inefficient to stimulate the skeletal muscle at the cardiac rate when the patient is at rest and requires only modest cardiac output. Similarly, it may be inefficient and even dangerous to stimulate skeletal muscle contraction at very high rates. The nature of the skeletal muscle stimulation may also be changed to improve efficiency over the range of available rates and cardiac demands.

SUMMARY OF THE INVENTION

One embodiment of the present invention employs a chronically implantable oximeter which is positioned within the skeletal muscle of a cardiac assist system it is preferably a two wave length reflectance oximeter which measures the relative oxygen level within the skeletal muscle as it powers the cardiac assist system. The two wavelength reflectance signal is sent to be processed within the implantable pulse generator of the cardiac assist system.

Circuitry which is internal to the implantable pulse generator determines the relative oxygen level and performs a trend analysis concerning the chronic sufficiency of the vascularization of and circulatory support to the skeletal muscle. This data is stored in memory within the implantable pulse generator. This memory may be interrogated by medical personnel using telemetry to obtain status and trend information concerning the cardiac assist system.

The data may be analyzed by medical personnel to determine the effectiveness of conditioning, the sufficiency of maintenance stimulation, the adequacy of vascularization, and the chronic prognosis for the cardiac assist system. This enables the medical personnel to manually modify the conditioning regimen, change the maintenance stimulation, institute various drug therapies, and plan for necessary surgical intervention.

In a second embodiment, a chronically biocompatible pressure transducer is implanted within the skeletal muscle tissue. This transducer produces electrical signals sufficient to enable an implantable pulse generator to measure the timing and extent of contraction and relaxation of the skeletal muscle in the performance of cardiac assistance.

The timing indications are important because they permit the implantable pulse generator to stimulate the skeletal muscle at the appropriate time to optimize the assist. For a configuration wherein the skeletal muscle is wrapped about the aorta, for example, contraction of the skeletal muscle should be delayed until immediately following contraction of the myocardium. Contraction of the skeletal muscle during the contraction of the myocardium will increase rather than decrease the load on the human heart. For skeletal muscle wrapped directly about the human heart, on the other hand, the stimulation should cause simultaneous contraction to achieve maximum benefit.

Measurement of timing and extent of skeletal muscle contractions permits the implantable pulse generator to monitor and control the conditioning regimen. This is important from a system viewpoint as it permits efficient energy utilization, as various phases of the conditioning process require the use of substantial stimulation energy. Such monitoring and control are important medically, because prior to complete conditioning, the skeletal muscle will readily fatigue, possibly resulting in excess loading of the myocardium.

An additional embodiment of the present invention employs a sensor to determine cardiac demand. Preferably this is an activity sensor although other types of sensors may be used, such as blood oxygen level. During periods of low demand, such as when the patient is at rest and the patient's heart requires little assistance, the duty cycle is lowered to improve overall efficiency. As cardiac demand increases, the duty cycle is increased ensuring that the patient's heart obtains greater assistance at higher loads. Above a very high rate, the duty cycle is again decreased to improve overall hemodynamic efficiency and as a safety measure.

The nature of the skeletal muscle stimulation is also changed with cardiac demand. At low demand levels, the number of pulses in a given burst and the amplitude are decreased to improve efficiency. As demand is increased, pulse count and amplitude are increased to increase the amount of cardiac assistance. Pulse count and amplitude are again decreased at excessively high cardiac rates as a safety measure.

A further embodiment of the present invention employs a chronically implantable temperature sensor which is positioned within the skeletal muscle of a cardiac assist system. The sensor preferably employs a thermo-resistive device, such as a thermistor, coupled to the implantable pulse generator of the cardiac assist system.

A circuit in the implantable pulse generator senses the changes in resistance of the thermistor which correspond to temperature changes within the skeletal muscle. The implantable pulse generator is thus able to monitor the efficiency of the work output of the skeletal muscle.

Circuitry within the implantable pulse generator changes the timing and characteristics of the generated pulses in relation to naturally occurring and paced heart contractions to optimize muscle activity. This improves the efficiency of the cardiac assist system by minimizing parasitic heat production. It also ensures that the myocardium obtains maximum assistance from contractions of the skeletal muscle.

Employing each of these embodiments of the present invention substantially improves the efficiency of the cardiac assist system through monitoring and control of the conditioning activity. Such monitoring and control also decreases the medical risk of the procedure.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 9 is a block diagram of an alternative embodiment of the implantable pulse generator;

DETAILED DESCRIPTION OF THE PREFERRED EMBODIMENTS

The present invention employs one or more sensors implanted within the skeletal muscle of a skeletal muscle-powered cardiac assist system to chronically monitor the adequacy of circulatory support. That is, the quantity of blood perfusion sufficient to prevent irreversible tissue damage. The cardiac assist system may be configured in a variety of ways as described in U.S. Pat. No. 4,813,952 issued to Khalafalla, herein incorporated by reference. Several of these configurations are discussed herein by way of illustration and are not intended to limit the present invention.

Figure 1:
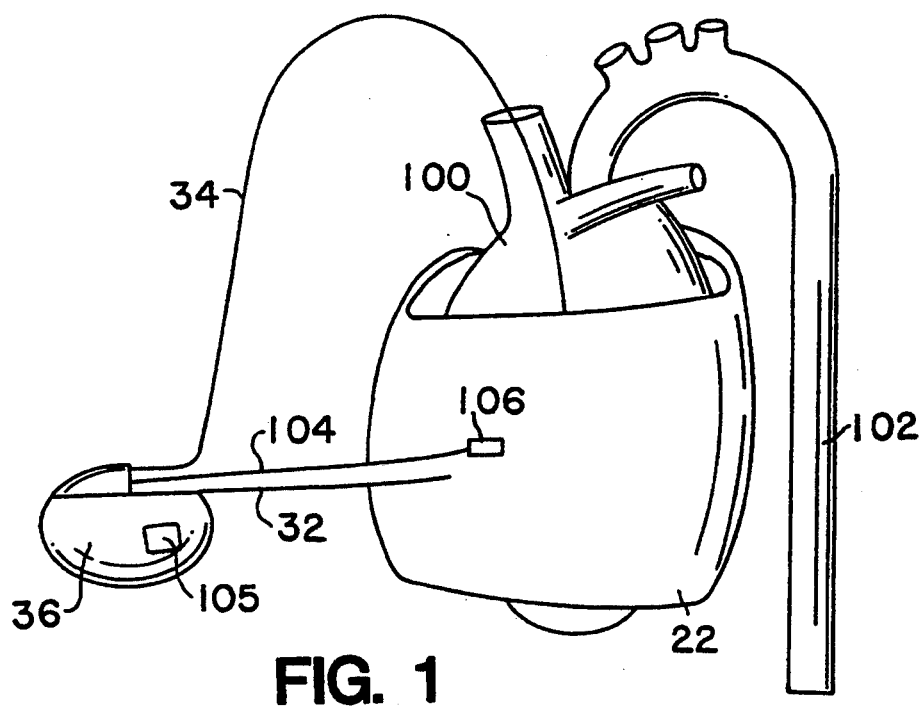
FIG. 1 is a first embodiment of the present invention wherein the skeletal muscle is wrapped about the myocardium.

FIG. 1 is an embodiment of the present invention wherein skeletal muscle 22 is wrapped about human heart 100. Skeletal muscle 22 is conditioned as a "slow twitch" muscle as described by Cox in U.S. Pat. No. 4,411,268, herein incorporated by reference. Implantable pulse generator 36 is coupled to pacing lead 34 to produce a demand pacemaker as taught by Cox. In addition, implantable pulse generator 36 stimulates skeletal muscle 22 to contract in synchrony with human heart 100. Assistance to human heart 100 is provided by the simultaneous contraction of skeletal muscle 22 to increase systolic pressure in descending aorta 102 and elsewhere in the circulatory system.

According to the present invention, a sensor 106 is implanted upon or within skeletal muscle 22 to determine the adequacy of chronic support by direct (e.g., colorimetry) or indirect (e.g., temperature, intramuscular pressure) measurement of a monitored parameter. A change from "red" to "blue" in muscle tissue is a direct indication of inadequate circulatory support, while the combination of a drop in muscle tissue temperature and a drop in intramuscular pressure points to the possibility of inadequate circulatory support. The data measured by sensor 106 is transferred to implantable pulse generator 36 via lead 104 where it is processed, stored, and may be telemetered percutaneously using normal implantable pulse generator telemetry circuitry for analysis by medical personnel.

According to the present invention, implantable pulse generator 36 may also employ activity sensor 105 in addition to the other sensors. The activity sensor input is used by implantable pulse generator 36 to adjust the various parameters of the skeletal muscle stimulation regimen as explained below. The parameters to be adjusted include duty cycle, and pulse width, amplitude, count and interval.

Figure 2:
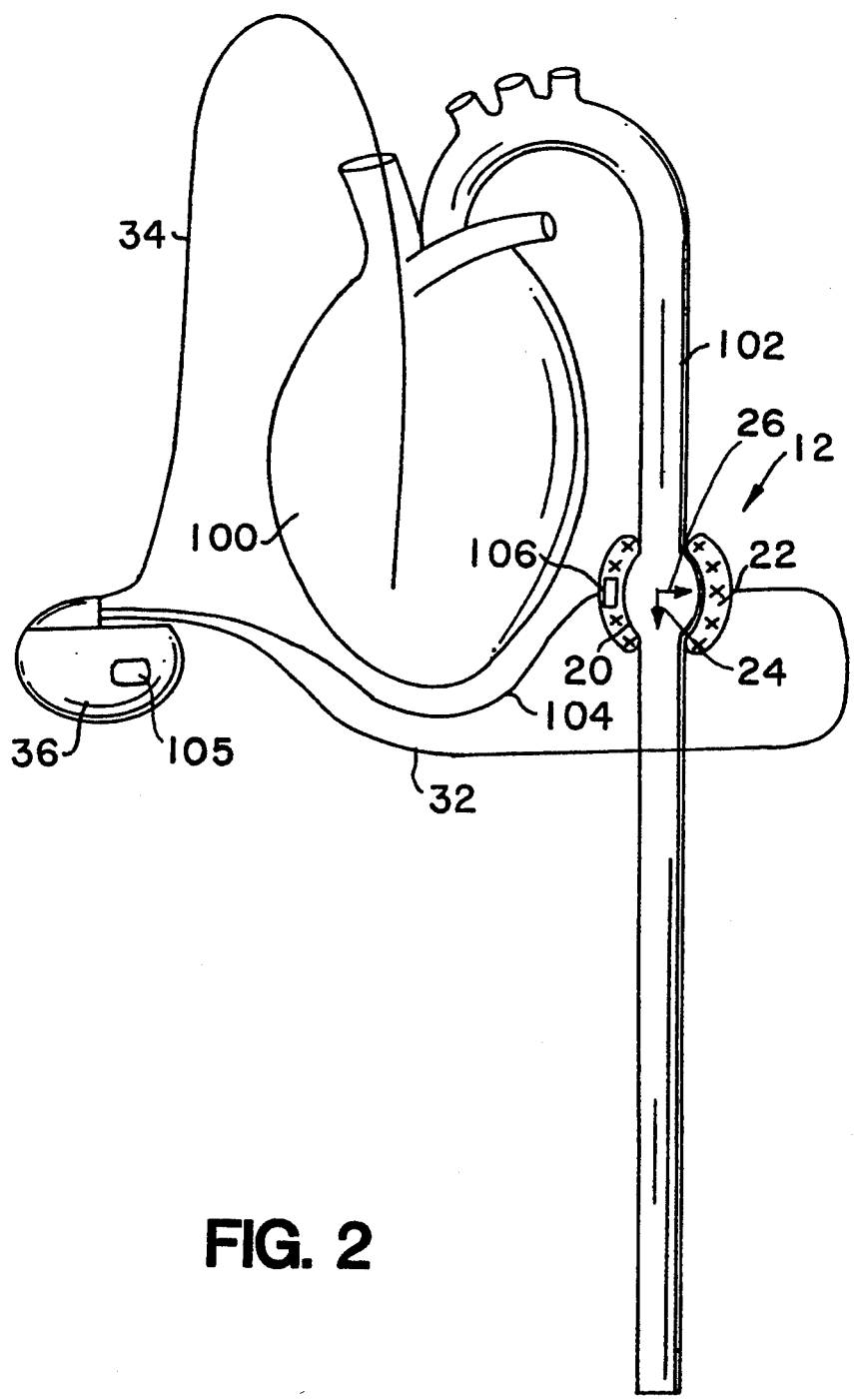
FIG. 2 is an alternative embodiment of the present invention wherein the skeletal muscle is wrapped about the descending aorta.

FIG. 2 is an alternative embodiment of the present invention. In this embodiment skeletal muscle 22 is wrapped about artificial chamber 20 inserted in series with descending aorta 102. Unlike the embodiment of FIG. 1, implantable pulse generator 36 stimulates skeletal muscle 22 to contract following evacuation of human heart 100. This is accomplished by the insertion of a delay between a paced or sensed beat of human heart 100 and the stimulation of skeletal muscle 22.

Figure 3:
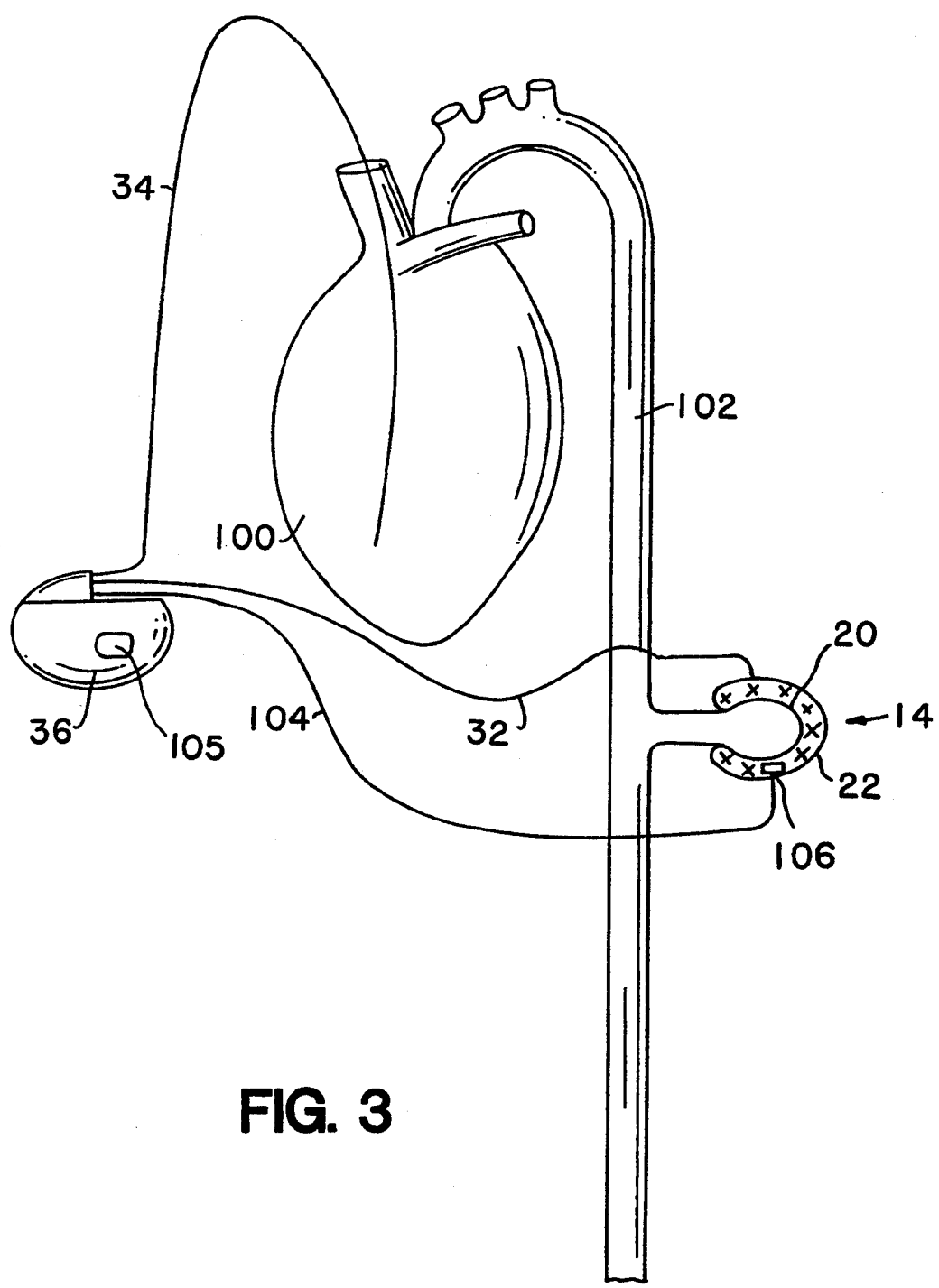
FIG. 3 is an alternative embodiment of the present invention wherein the skeletal muscle performs counter pulsation of the descending aorta.

FIG. 3 is a further embodiment wherein artificial chamber 20 is coupled external to descending aorta 102. In this configuration skeletal muscle 22 is stimulated to counter pulse human heart 100. This raises diastolic pressure, thereby increasing perfusion of human heart 100. This is accomplished by the insertion by implantable pulse generator 36 of a sufficient delay between a sensed or paced contraction of human heart 100 and stimulation of skeletal muscle 22 to cause the desired counter pulsation.

Figure 4:
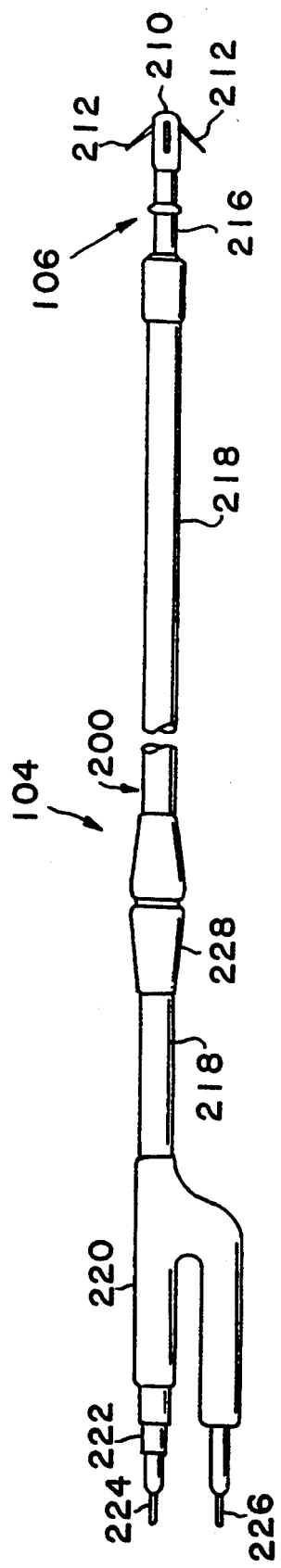
FIG. 4 is a plan view of an oximetry probe.

FIG. 4 is a plan view of lead 104 wherein sensor 106 employs an oximeter for measuring adequacy of oxygen level within skeletal muscle 22. It is estimated that a 30 to 50 percent decrease in oxygen level may be sufficient to cause irreversible muscle tissue damage. U.S. Pat. No. 4,813,421 issued to Baudino, et al., herein incorporated by reference, describes in greater detail the preferred embodiment of an oximeter probe within sensor 106 and lead 104.

Lead 104 is a typical chronically implantable lead. It contains an insulated bifurcated proximal connector assembly 220 which sealingly plugs into implantable pulse generator 36. The proximal end of connector assembly 220 contains terminal pins 224 and 226. A third conductor within lead 104 is terminated at ring terminal 222. The main body of lead 104 is covered with biocompatible outer sheath 218 of silicone rubber or polyurethane. Anchoring sleeve 228 facilitates securing of the proximal end of lead 104 in the manner well-known in the art.

The distal end 210 of lead 104 contains sensor 106 which is preferably a two wavelength reflectance oximeter as taught by Baudino, et al. Maintenance of the position of sensor 106 may be facilitated by tine members 212 which work particularly well for positioning of transvenous pacing leads as is well-known in the art. Oximetry structure 216 is positioned near distal end 210. Oximetry structure 216 is covered with synthetic sapphire as taught by Baudino, et al.

Figure 5:
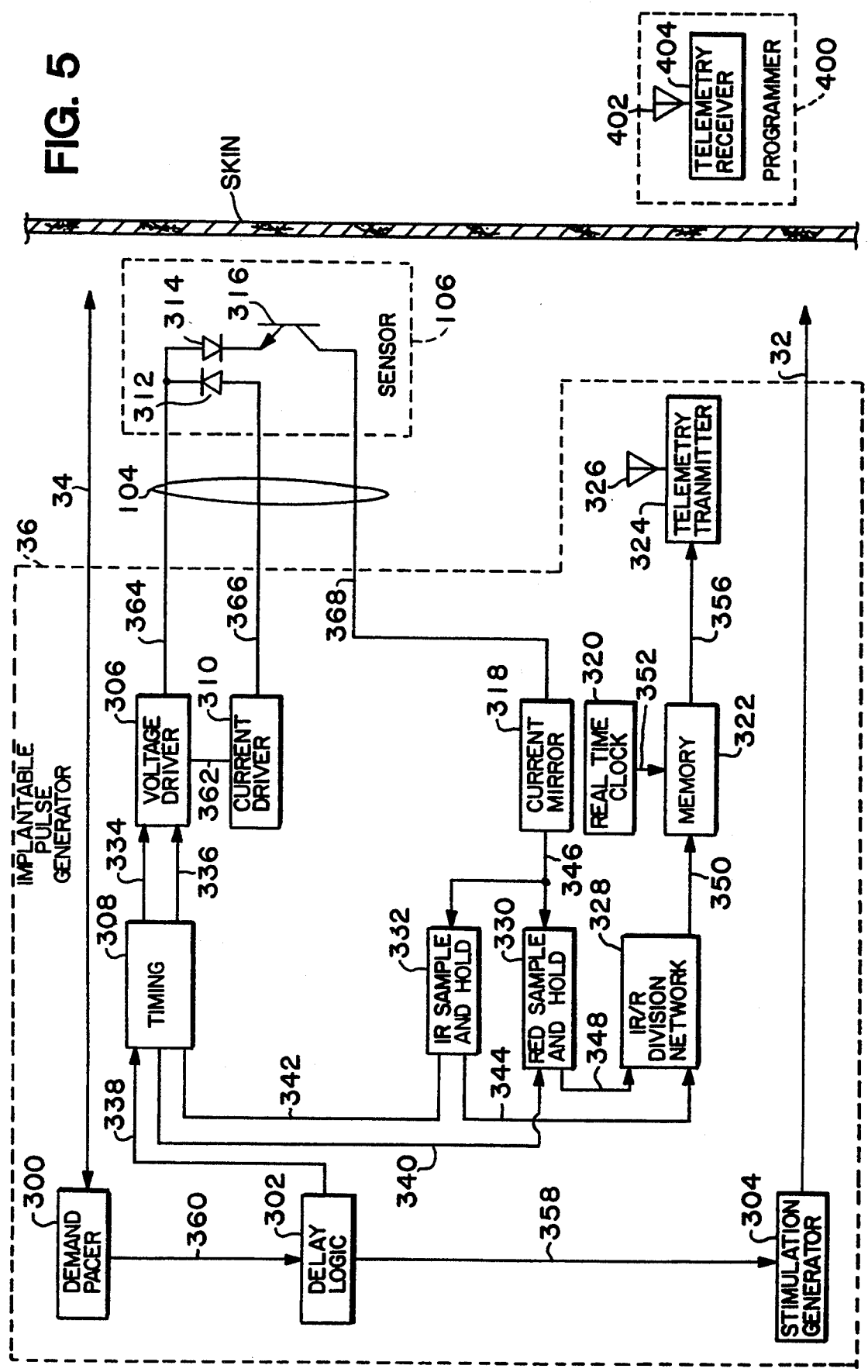
FIG. 5 is a block diagram of a implantable pulse generator.

FIG. 5 is an overall block diagram of the circuitry within implantable pulse generator 36 for embodiments employing an oxygen sensor. Demand pacer 300 is constructed according to circuitry known in the art of pacing and communicates with human heart 100 via lead 34. Demand pacer 300 notifies delay logic 302 via line 360 of a contraction of human heart 100. This may be the result of either a sensed natural heart contraction or an artificially generated pacing pulse. In either situation, delay logic 302 generates a delay appropriate to the particular embodiment (see above) and signals stimulation generator 304 by line 358 to stimulate skeletal muscle 22 via lead 32. Stimulation generator 304 may also contain muscle conditioning circuitry, which is not shown for clarity. U.S. Pat. No. 4,411,268 issued to Cox should be consulted for a more detailed description of skeletal muscle conditioning. Delay logic 302 also provides timing 308 with a begin sensing signal via line 338. This begin sensing signal is synchronous with the contraction of human heart 100 and delayed from it so that motion artifacts are minimized during the sensing process.

Timing 308 notifies voltage driver 306 via lines 334 and 336 when to energize infrared LED 312 and red LED 314, respectively. Current driver 310, coupled via common line 362 to voltage driver 306, maintains the illumination of each LED to enable photosensor 316 to measure the reflected return. Infrared LED 312, red LED 314, and photosensor 316 are all located within sensor 106 and coupled to implantable pulse generator 36 by lead 104 as shown. Lines 364, 366, and 368 comprise the three conductors of lead 104 (see also FIG. 4).

The sensed return of photosensor 316 is transferred to current mirror 318 via line 368 for processing. After processing, the resultant is transferred to IR sample and hold 332 and red sample and hold 330 by line 346. The signal is gated to the proper sample and hold circuit by timing 308 using gating signals on lines 340 and 342.

IR/RR division network 328 compares the infrared and red signals received via lines 344 and 348 to sense color shifts. The periodic sensor outputs of IR/R division network 328 are sent by line 350 to memory 322 for storage awaiting readout by medical personnel. Each measured signal is time tagged by the output of real time clock 320 on line 352.

Medical personnel can access the time-tagged sensor data stored in memory 322 by telemetry techniques common in the implantable device field. Preferably this access is via a radio frequency signal prepared by telemetry transmitter 324 as modulated with data received on line 356 from memory 322. This radio frequency signal is transmitted by radio frequency antenna 326. The signal is received outside of the body by antenna 402, demodulated by telemetry receiver 404 and processed and presented to medical personnel by programmer 400 in the manner known in the art.

An alternative implementation of implantable pulse generator 36 is through the use of a microprocessor controlled general purpose implantable pulse generator such as Prometheus ™ pulse generator manufactured by Medtronic, B.V. of the Netherlands. The primary advantage of such an implementation is the ease with which such a programmable device can change modes of operation. This is particularly useful when doing clinical research. A description of the use of such a device may be found in the paper "Pulse Generator for Biomechanical Cardiac Assistance by Counter-Pulsation Technique" by Grandjean, et al , published in the "Record of the Conference on Skeletal Muscle for Cardiac Assist and Repair, Banff Sept 28–Oct. 2 1988", published by Futura Editions (August 1989) and in "Transformed Skeletal Muscle for Cardiac Assist and Repair", edited by R. Chiu and I. Bourgeois, (August 1989).

Figure 6:
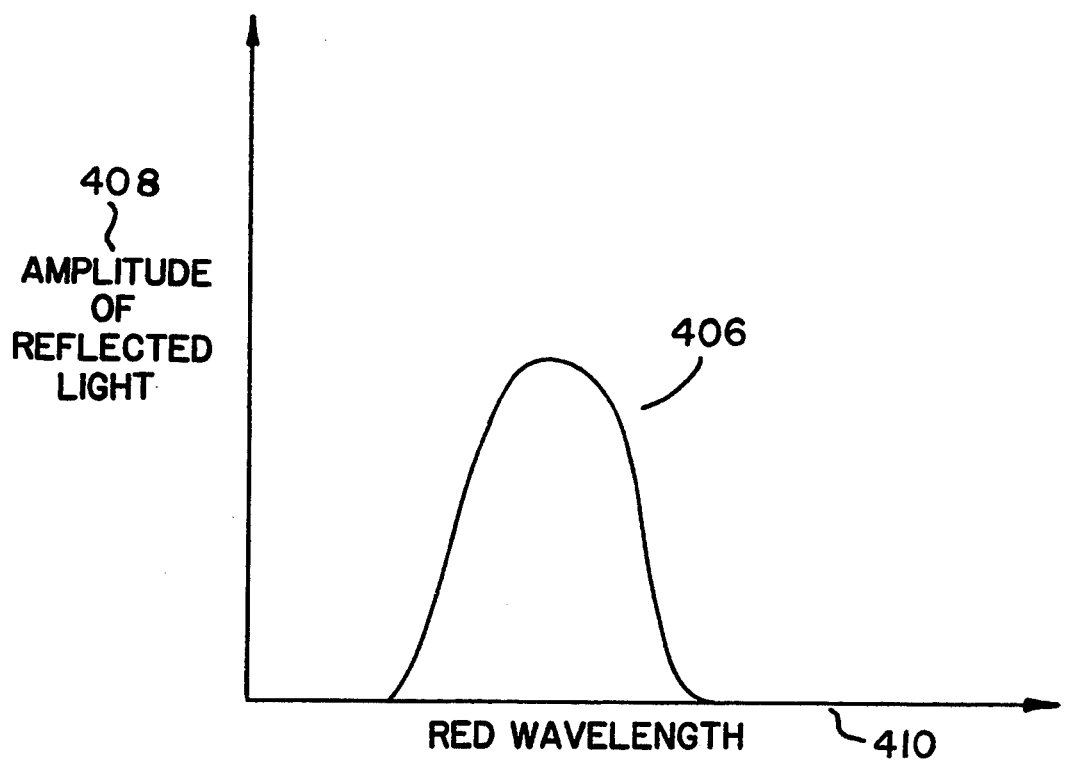
FIG. 6 is a graphical representation of the oximetry return in an oxygen sufficient environment.

FIG. 6 is a graphical representation 406 of the sensed signals from a skeletal muscle 22 which is adequately supported by the vascular system. The amplitude of the reflected light 408 is relatively sharply peaked within the region of visible red wavelengths 410. This indication when read from memory 322 via telemetry indicates that skeletal muscle 22 was receiving sufficient support for its work-load at the time tag of the sensor reading. A complete series of such signals stored within memory 322 verifies that skeletal muscle 22 continues to be healthy.

Figure 7:
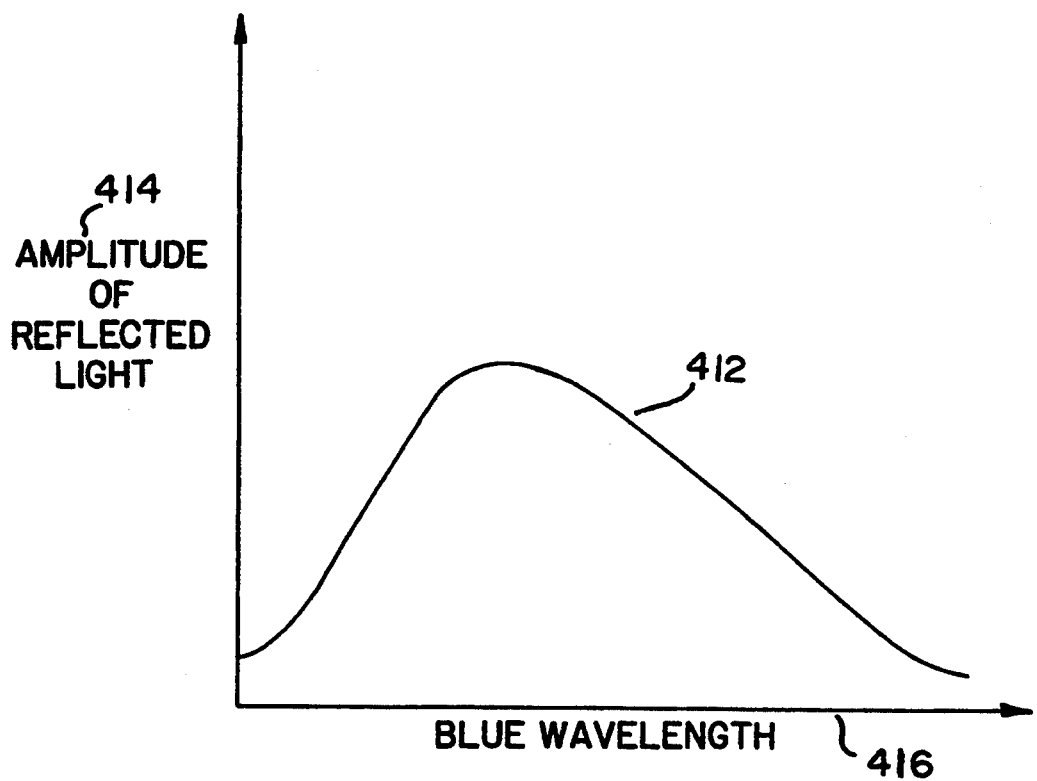
FIG. 7 is a graphical representation of the oximetry return in an oxygen insufficient environment.

FIG. 7 shows the response 412 of sensor 106 when skeletal muscle 22 is not adequately supported by the vascular system. As can be seen, the amplitude of reflected light 414 is shifted to the blue wavelengths 416 and is not sharply defined. Medical personnel upon seeing this indication from memory 322 will conclude that skeletal muscle 22 is not receiving sufficient oxygen for its workload. Continuation of this state indicates a high risk of ischemia to a portion or all of skeletal muscle 22.

Immediate medical action includes reduction of the physical load on skeletal muscle 22 by reducing the duty cycle of stimulation pulses. Total cessation of stimulating pulses will place skeletal muscle 22 at rest without any load. Skeletal muscle 22 may respond to additional conditioning as taught by Cox. In severe cases, surgical intervention may be required.

Figure 8:
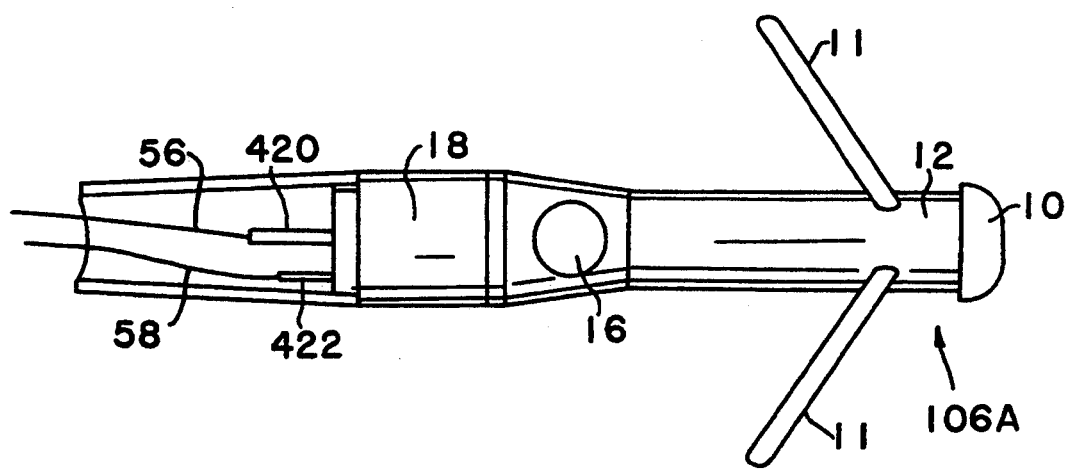
FIG. 8 is a plan view of an implantable pressure transducer.

FIG. 8 is a plan view of sensor 106A employing a chronically implantable pressure transducer within sensor 106A. This pressure transducer is preferably of the type disclosed in U.S. Pat. No. 4,485,813 issued to Anderson, et al., herein incorporated by reference. The pressure transducer is piezoelectric. Piezoresistive pressure sensors are disclosed in U.S. Pat. No. 4,407,296 issued to Anderson and U.S. Pat. No. 4,432,372 issued to Monroe, also incorporated by reference.

Pressure sensor 106A has a distal tip 10 at the end of hollow and rigid shank 12. Tines 11 are appended to aid in attachment. These work particularly well with transvenous pacing leads. However, different attachment means may be more appropriate depending upon the exact nature of the skeletal muscle used. The pressure capsule 18 is hermetically sealed. Bore 16 provides fluid communication with pressure capsule 18. Because pressure capsule 18 uses a piezoelectric element, incident forces present produce a voltage across terminals 420 and 422. This signal is coupled to implantable pulse generator 36A via conductors 56 and 58 which run the length of lead 104.

FIG. 9 is a block diagram of implantable pulse generator 36A incorporating circuitry for processing the output of the pressure transducer. The implantable pulse generator 36A contains two basic portions. The first of these is primarily a demand pacemaker 110, which is readily known in the art. Its components include terminal 114, which couples transvenous lead 34 to sense amplifier 112 via line 115 and also directs artificial pacing pulses from pulse generator 113 to the myocardial tissue. Sense amplifier 112 attempts to detect naturally occurring heartbeats. If one is found, the artificial pacing pulse is inhibited.

Skeletal muscle 22 is coupled to implantable pulse generator 36A via terminal 121 which couples to electrical lead 32 to deliver the electrical stimulation energy. This stimulation energy is supplied by pulse generator 120. The signals used to condition skeletal muscle 22 are generated by conditioning generator 122 and supplied to terminal 121. The generation of such conditioning signals is discussed more extensively in U.S. Pat. No. 4,411,268, issued to Cox, which is incorporated herein by reference.

Feedback on the conditioning process is sensed by pressure sensor 106A and transferred to sensor processing 107 which processes the signal in a manner described below. This processed sensor signal is transferred via line 108 to sensor logic 109 which determines the degree of conditioning yet required using the technique described below. When the conditioning process is complete, sensor logic 109 notifies conditioning generator 122 via line 124 to produce the maintenance signals described below.

Sensor logic 109 also notifies logic 119 via line 125 of the timing of the actual contraction of skeletal muscle 22. This permits logic 119 to properly time the stimulation signal to skeletal muscle 22 as explained below.

Trigger circuit 123 and OR-gate 118 function as described by Cox to time the generation of the stimulation pulse to skeletal muscle 22 in relation to the contraction of human heart 100. A discussion of this timing for the various embodiments may be found below.

Figure 10C:
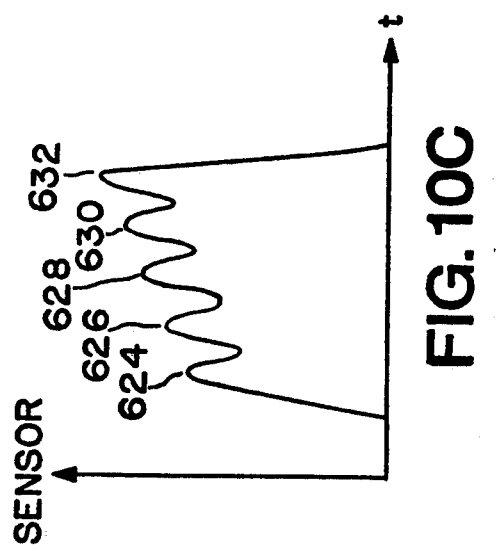
FIG. 10C is the waveform of the contraction as viewed by the pressure sensor.
Figure 10D:
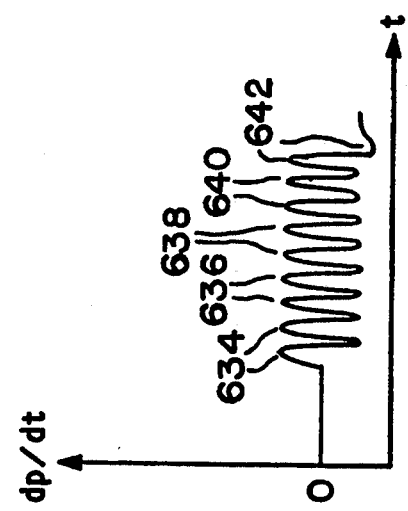
FIG. 10D is the differentiated pressure sensor signal showing that the skeletal muscle is unconditioned.
Figure 10A:
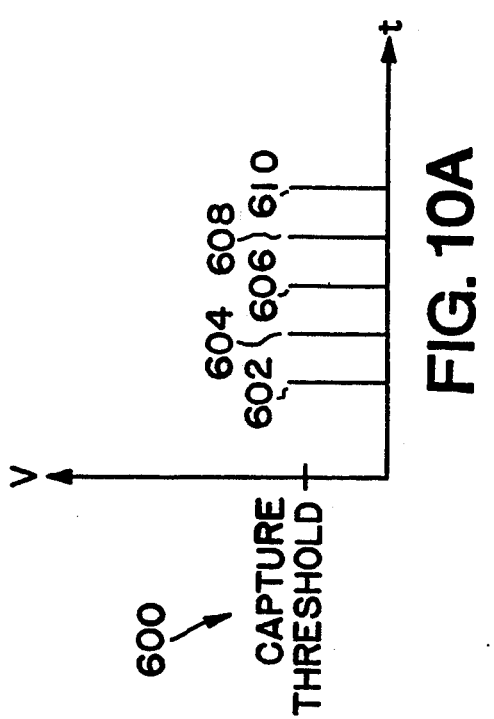
FIG. 10A is a graph of stimulation pulses applied to the unconditioned muscle.

FIG. 10A shows the stimulation patterns used to perform the conditioning. Skeletal muscle stimulation is different from cardiac stimulation in that the skeletal muscle does not have an all or nothing response to the electrical stimulus as does the myocardium. The skeletal muscle exhibits a gradual recruitment of fibers with increases in pulse amplitude and pulse width. Threshold for skeletal muscle 22 is the pulse amplitude/width needed to start muscle force recruitment. Pulse 602 is the stimulation pulse produced by pulse generator 120. It is generated to occur at the correct time in relation to the contraction of human heart 100. To be effective in causing contraction of skeletal muscle 22, pulse 602 must have a voltage greater than capture threshold 600. Pulses 604, 606, 608, and 610 are conditioning pulses produced by conditioning generator 122. The pulse rate is dependent upon the specific nature of skeletal muscle 22 as taught by Cox, but it is typically in a range of 20–30 hz. To optimally perform conditioning, pulses 604, 606, 608, and 610 have a voltage in excess of capture threshold 600.

Figure 10B:
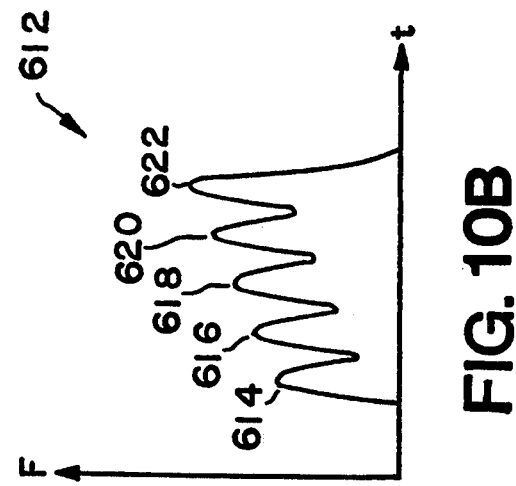
FIG. 10B is the contraction pattern resulting from the stimulation of FIG. 6A.

FIG. 10B shows the response of unconditioned skeletal muscle 22 to receipt of pulses 602, 604, 606, 608, and 610. Notice that each produces a contractile force 614, 616, 618, 620, and 622, respectively. This occurs with unconditioned muscles which are known as "fast-twitch" muscles. A more detailed explanation may be found in the Cox reference.

FIG. 10C shows the response of pressure sensor 106A to the contractions of FIG. 10B. These result in pressure peaks 624, 626, 628, 630, and 632, respectively.

FIG. 10D shows the result of differentiation by sensor processing 107 of the sensor signal of FIG. 10C. This differentiation produces sharp peak pairs 634, 636, 638, 640, and 642, respectively, indicating the inflection points. From this waveform, a simple analog filter and detector known to those in the art could easily determine that skeletal muscle 22 is unconditioned.

Figure 11C:
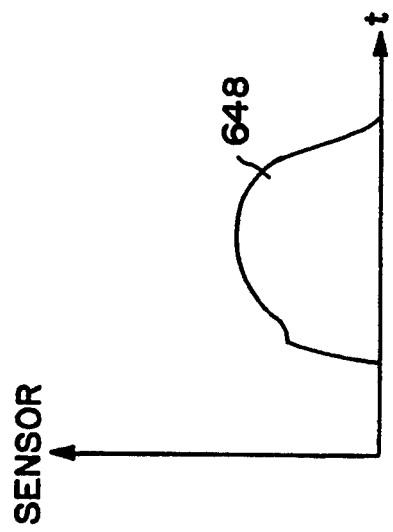
FIG. 11C is the waveform of the contraction as viewed by the pressure sensor.
Figure 11D:
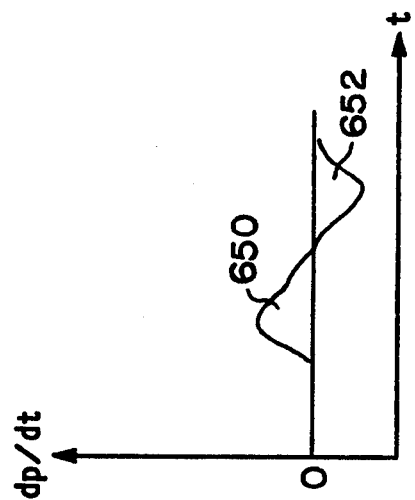
FIG. 11D is the differentiated pressure sensor signal showing that the skeletal muscle is fully conditioned.
Figure 11A:
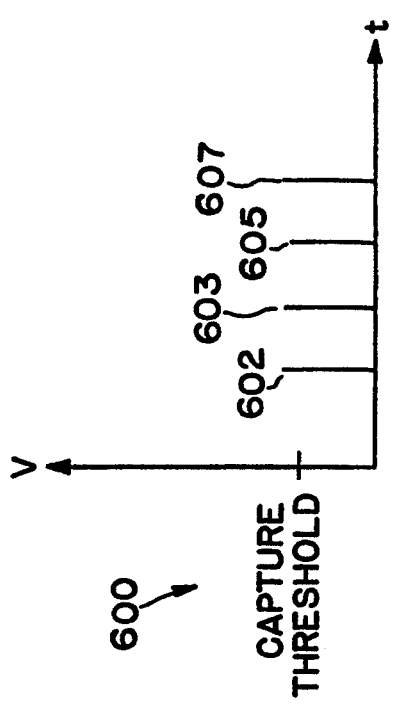
FIG. 11A is a graph of stimulation signals applied to the conditioned muscle.
Figure 11B:
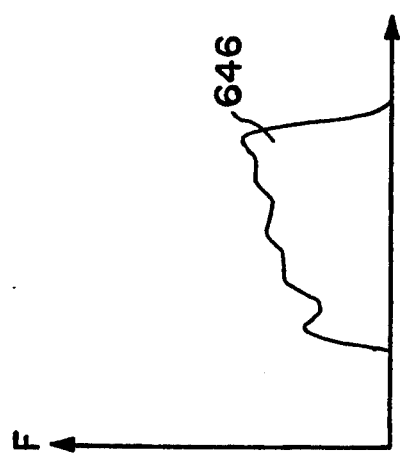
FIG. 11B is the contraction pattern resulting from the stimulation of FIG. 11A.
Figure 12:
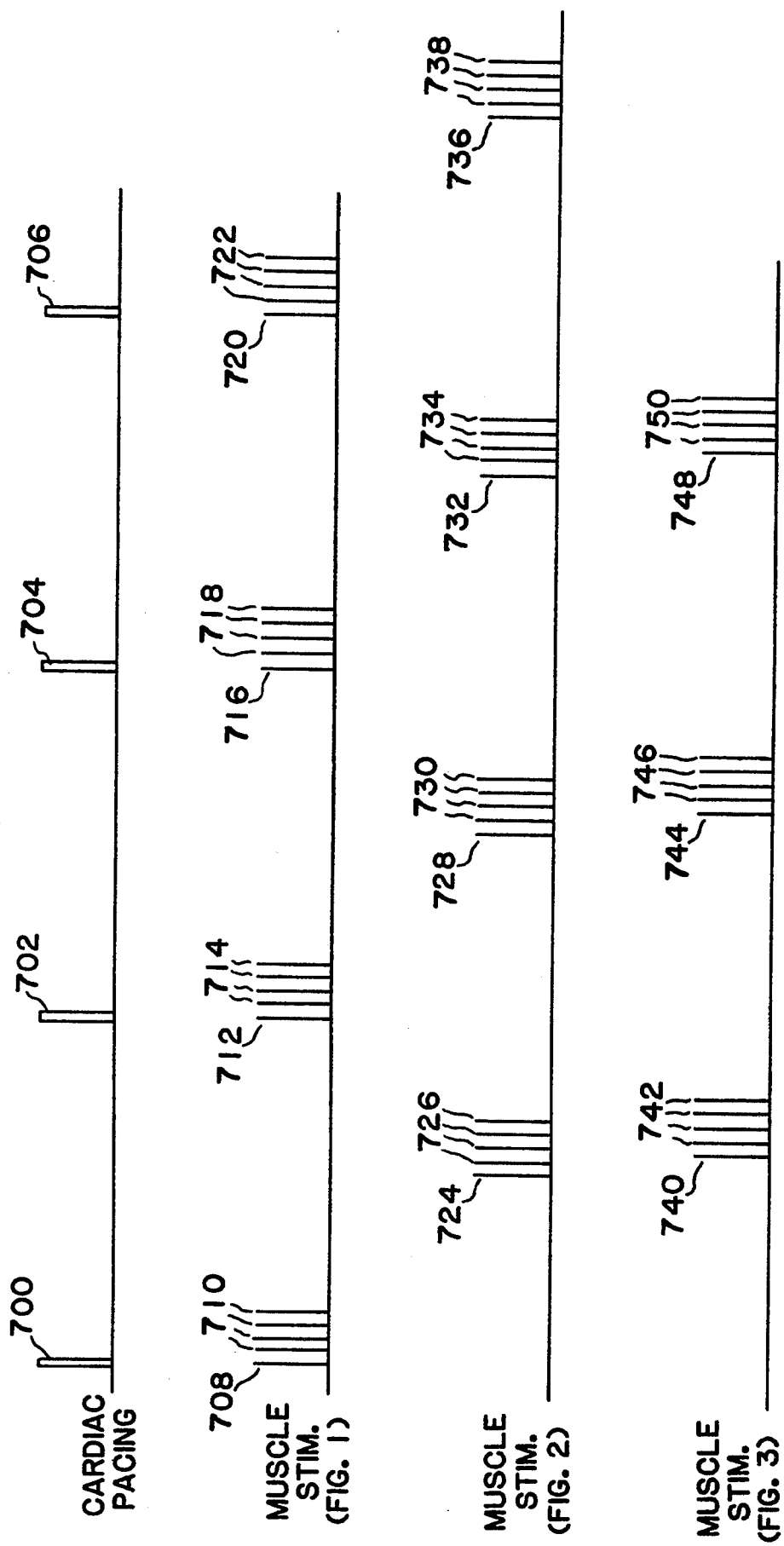
FIG. 12 shows the timing relationship between the cardiac pacing pulse and skeletal muscle stimulation signals for the embodiments of FIGS. 1, 2, and 3.

FIGS. 11A 11B, 110, and 11D show the corresponding waveforms for skeletal muscle 22 after complete conditioning. When presented with the stimulation pattern of FIG. 10A, the contractile response is shown in FIG. 11B as waveform 646. Notice that individual conditioning pulses no longer produce major contractile peaks. This occurs because skeletal muscle 22 has been conditioned to act as a "slow-twitch" muscle, similar to myocardial tissue. When the conditioned response of FIG. 11B is sensed by pressure sensor 106A, the resulting waveform 648 of FIG. 11C is produced. This results in the differentiated waveform of FIG. 11D after processing by sensor processing 107. This represents but two inflection points as excursions 650 and 652. Again this becomes easily recognizable as a skeletal muscle 22 which is fully conditioned.

FIG. 11A shows the stimulation pattern used after skeletal muscle 22 is fully conditioned. Pulse 602 has a voltage in excess of capture threshold 600. This pulse which is produced by pulse generator 120, stimulates the contraction of skeletal muscle 22. Conditioning pulses 604, 606, 608, and 610 (see also FIG. 10A) produced by conditioning generator 122 have been replaced by maintenance pulses 603, 605, 607, and 609, respectively. The maintenance pulses must yet have a voltage greater than capture threshold 600. However, because of the smoother contraction pattern of the conditioned skeletal muscle, pulse width, pulse amplitude, pulse spacing and pulse number can be safely adjusted to save energy. Conditioning generator 122 switches from conditioning pulses to maintenance pulses in response to a notification of a conditioning accomplished signal from sensor logic 109 via line 124.

Figure 21:
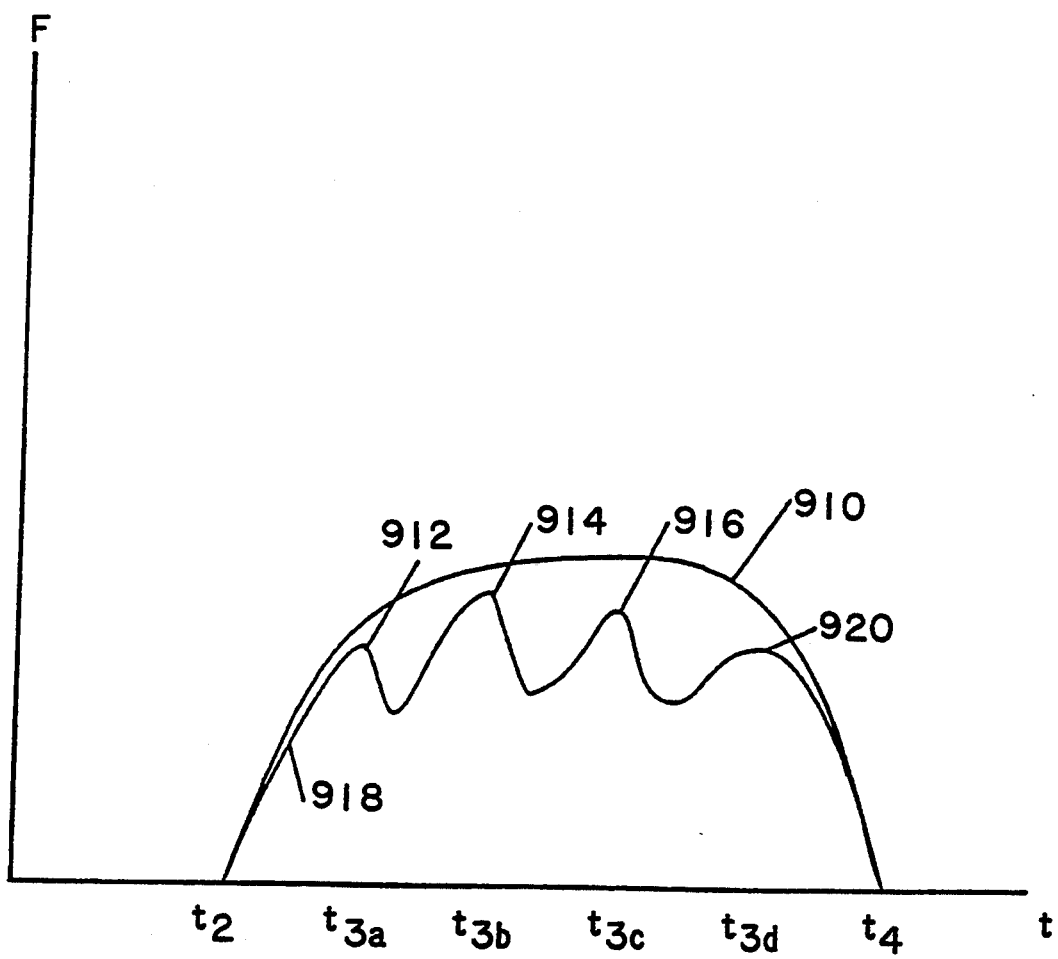
FIG. 21 is a graphical representation of the force produced by conditioned and unconditioned skeletal muscle.

FIG. 21 shows the timing relationship between stimulation of the myocardium and stimulation of skeletal muscle 22 for the various embodiments of FIGS. 1, 2, and 3. For simplicity it is assumed that all myocardial contractions are artificially stimulated by pacing pulses 700, 702, 704, and 706 at a fixed rate. These might also be natural contractions which inhibit the pacing pulse, but the rate would then not be constant.

For the embodiment of FIG. 1, it is desired that human heart 100 and skeletal muscle contract simultaneously. Therefore, stimulating pulses 708, 712, 716, and 720 occur at the same time as pacing pulses 700, 702, 704, and 706, respectively. Maintenance pulse groups 710, 714, 718, and 722 occur as explained above. The timing for this embodiment is easily accomplished for paced beats of human heart 100, since the timing is coincident. For sensed beats (i.e., the artificial pacing pulses are inhibited), stimulating pulses 708, 712, 716, and 720 are generated immediately upon sensing a naturally occurring R-wave.

Skeletal muscle 22 is stimulated by pulses 724, 728, 732, and 736 for the embodiment of FIG. 2. These are delayed for a period following the corresponding pacing pulse (or sensed R-wave) sufficient to enable human heart 100 to empty. Contraction of skeletal muscle 22 too soon will increase the load on human heart 100. A delay which is too long will cause skeletal muscle 22 to pump less than the optimal quantity of blood. The exact delay is easily measure by pressure sensor 106A as explained above. The delay may be made a function of rate, stroke volume, etc. It may be determined empirically by medical personnel or simply programmed to the nominal values known in the art.

Stimulation pulses 740, 744, and 748 cause skeletal muscle 22 to counterpulse the descending aorta. This increases the total perfusion through the coronary system, thereby assisting human heart 100. These pulses are timed to occur approximately one-half heart cycle after contraction of human heart 100.

Figure 13:
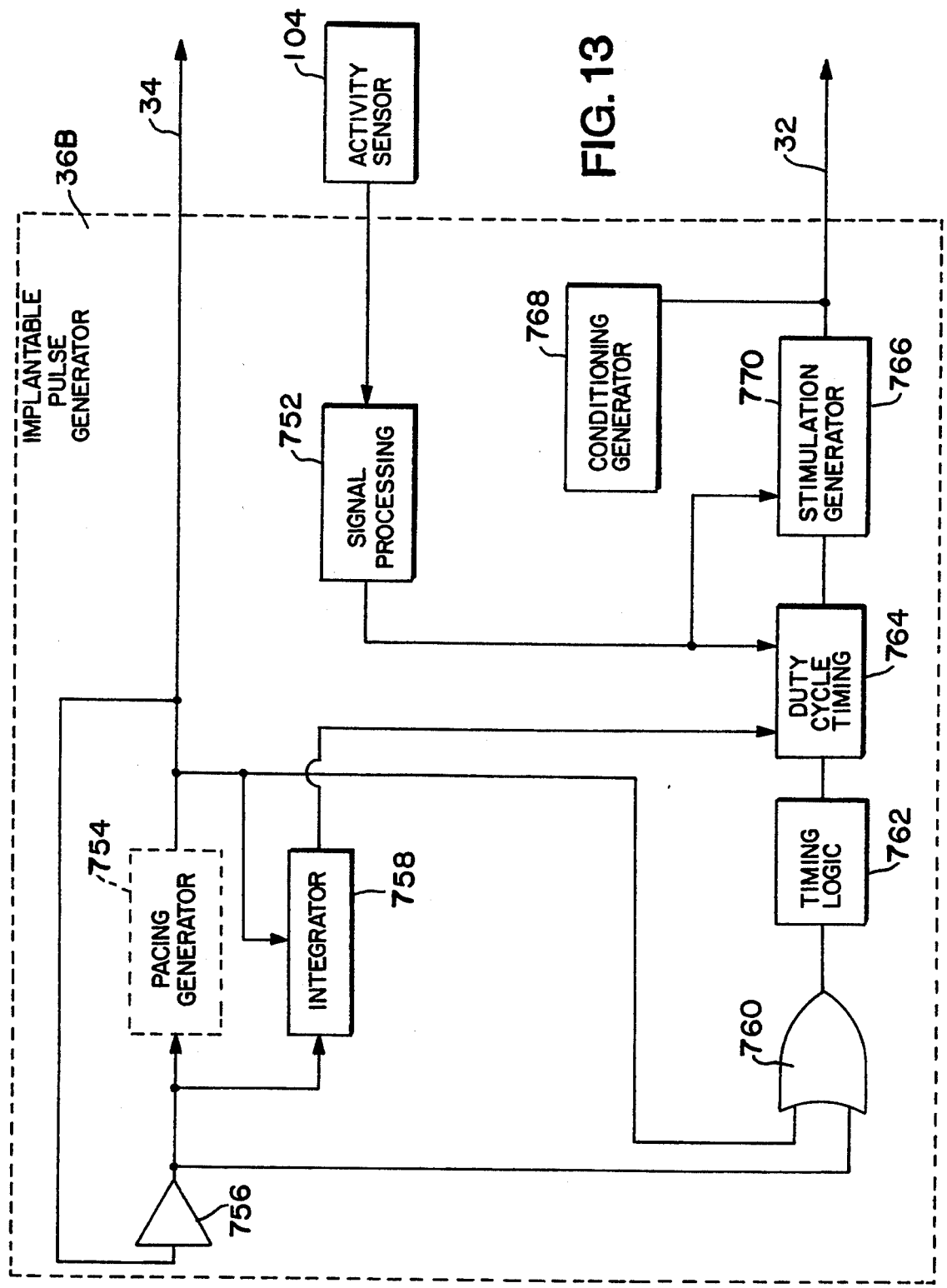
FIG. 13 is a block diagram of an alternative embodiment of the implantable pulse generator.

FIG. 13 is a block diagram of implantable pulse generator 36B having circuitry for processing the output of activity sensor 105. It includes a pacing generator 754 which operates in the demand mode as is known in the art. Basically, the electrical activity of the patient's heart is monitored via pacing lead 34. Whenever a naturally occurring contraction of the heart is found, sense amplifier 756 detects it and notifies pacing generator 754. If this naturally occurring contraction is sensed within the allotted time, the output of pacing generator 754 is inhibited. However, if pacing generator 754 determines that sufficient time has elapsed since the last contraction of the heart, it produces a pulse which is conveyed to the heart via pacing lead 34 to artificially stimulate the desired contraction.

The main purpose of stimulation generator 766 is to produce a burst of pulses to cause contraction of skeletal muscle 22 in the proper timing relation to the contraction of the patient's heart. To do so, OR-gate 760 produces an output whenever sense amplifier 756 senses a naturally occurring contraction or pacing generator 754 supplies an artificial pacing pulse. In either situation, timing logic 762 is started to generate the desired amount of delay. This delay is nearly zero for the embodiment of FIG. 1, because maximum assistance to the myocardium is provided when skeletal muscle 22 contracts at the same time as the heart.

The embodiment of FIG. 2 requires a much longer delay. This period is on the order of one-half of the cardiac cycle (i.e. R-to-R interval). The embodiment of FIG. 3 requires yet a slightly longer delay, being somewhat greater than one-half of the cardiac cycle. This is necessary because this embodiment is intended to increase diastolic pressure in the aorta.

The output of timing logic 762 is a pulse which is synchronous with the naturally sensed or artificially stimulated contraction of the patient's heart but delayed in time according to the specific embodiment as described above. This pulse is supplied to duty cycle timing circuit 764. This circuit is simply a variable digital counter which produces an output corresponding to a variable number of pulses received from timing logic 762. The normal output of duty cycle timing circuit 764 is one pulse for each pulse received from timing logic 762. This corresponds to the one-for-one stimulation mode of skeletal muscle 22. A lesser ratio of output pulses to input pulses is determined by overall cardiac rate and anticipated cardiac demand.

Overall cardiac rate is determined by integrator 758. It is a circuit which receives inputs from both sense amplifier 756 and pacing generator 754, much as with OR-gate 760. In this way integrator 758 is notified of both naturally occurring and artificially paced contractions of the patient's heart. Integrator 758 simply integrates these two signals to produce an average current heart rate. This signal is sent to duty cycle timer circuit 764 to adjust the variable rate counter in a manner which is described in more detail below.

The anticipated cardiac demand may be determined in a number of ways known in the art of cardiac pacing. These include, without limitation, measurement of venous blood oxygen level, measurement of blood ph, determination of respiratory rate, computation of minute volume, and measurement of stroke volume. The preferred mode of the present invention uses an activity sensor such as found in Medtronic Activitrax ® pacemakers. Those of skill in the art will readily be able to substitute yet other sensors to determine anticipated cardiac demand.

In the preferred embodiment, an activity sensor 105 is mounted permanently to the housing of implantable pulse generator 36B. This activity sensor is preferably a piezoelectric crystal which converts mechanical energy received at the housing of implantable pulse generator 36B to electrical energy. It has been shown in the literature that activity sensing in this way is a very good means for anticipating cardiac demand. The output of activity sensor 105 is amplified and integrated by signal processing circuit 752. The result is a signal indicative of anticipated cardiac demand which is transferred to duty cycle timing circuit 764.

The output of duty cycle timing circuit 764 is a pulse train which is a variable number of counts of the output of timing logic 762. The exact relationship is described in more detail below. Stimulation generator 766 receives the output of duty cycle timing circuit 764 and generates an output burst of energy corresponding to each of the output pulses of duty cycle timing circuit 764. The number of pulses in this burst is determined in part by the output of signal processor 752 such that additional pulses are added to the burst when the anticipated cardiac demand becomes high.

Conditioning generator 768 supplies conditioning pulses as needed. The stimulation pulses of stimulation generator 766 are combined with the conditioning pulses of conditioning generator 768 and supplied to skeletal muscle 22 by stimulation lead 32.

Figure 14:
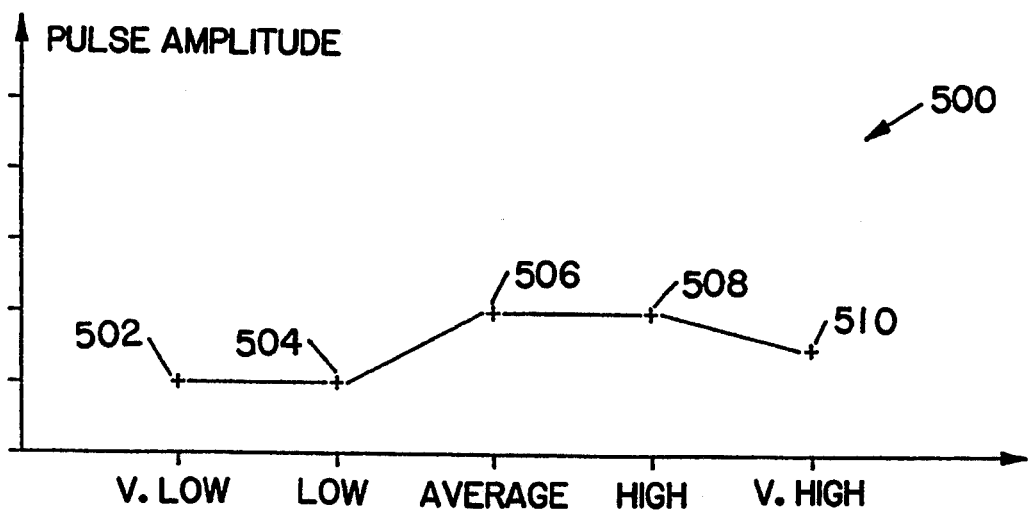
FIG. 14 is a graphical representation of pulse amplitude as a function of activity level.

FIG. 14 is a graphical representation of a relationship between the pulse amplitude and the anticipated cardiac demand. In this case anticipated cardiac demand corresponds to the appropriate cardiac rate which is determined from the output of activity sensor 105. This is computed in the manner known in the art from U.S. Pat. No. 5,479,402 issued to Anderson, et al. As can be seen, points 502 and 504 correspond to very low and low anticipated cardiac demand, respectively. These are on the order of less than 70 beats per minute. At these rates, stimulation generator 766 supplies output pulses of minimum amplitude. These pulses must be greater than the stimulation threshold of skeletal muscle 22. However, considerable energy is saved through using an amplitude which is only slightly greater than this threshold.

Points 506 and 508 correspond to average and high anticipated cardiac demand, respectively. These correspond to rates in the range of 70 to 120 beats per minute although the exact values are patient dependent. At this demand level, the cardiac loading is sufficient to benefit from the additional amplitude and therefore additional assurance of capture. Point 510 is above 120 pulses per minute for most patients. Again notice that this is the anticipated cardiac demand and not the actual heart rate.

Figure 15:
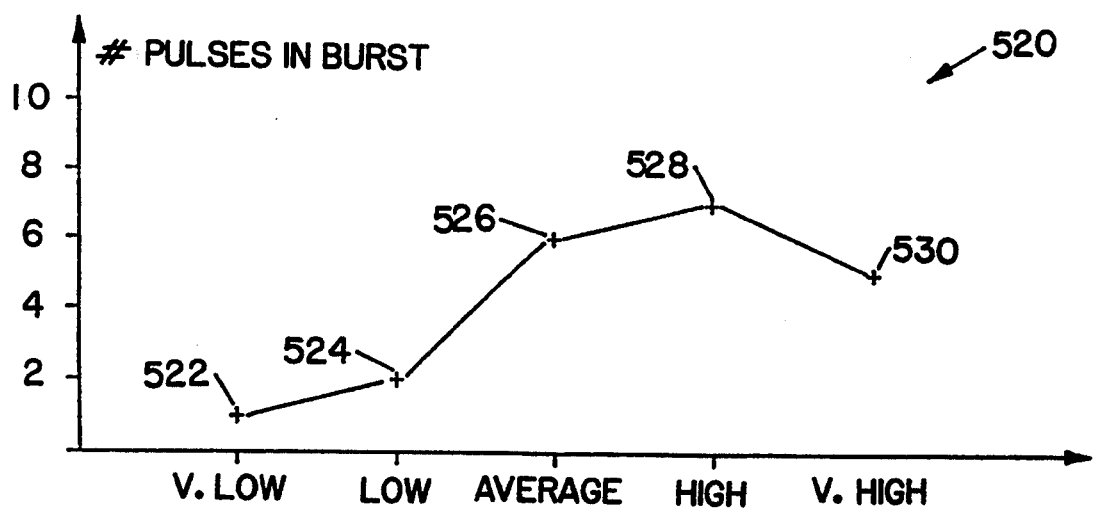
FIG. 15 is a graphical representation of pulses per burst as a function of activity level.

FIG. 15 is a graphical representation of the number of pulses in a given stimulation burst as a function of anticipated cardiac demand. The ranges along the abscissa are as explained above for most patients. Average and high anticipated cardiac demand again require the greatest number of pulses per burst and therefore the highest energy demand. The number of pulses per burst is decreased at very high anticipated demands because efficiency is impaired if the individual pulses occur too frequently.

Figure 16:
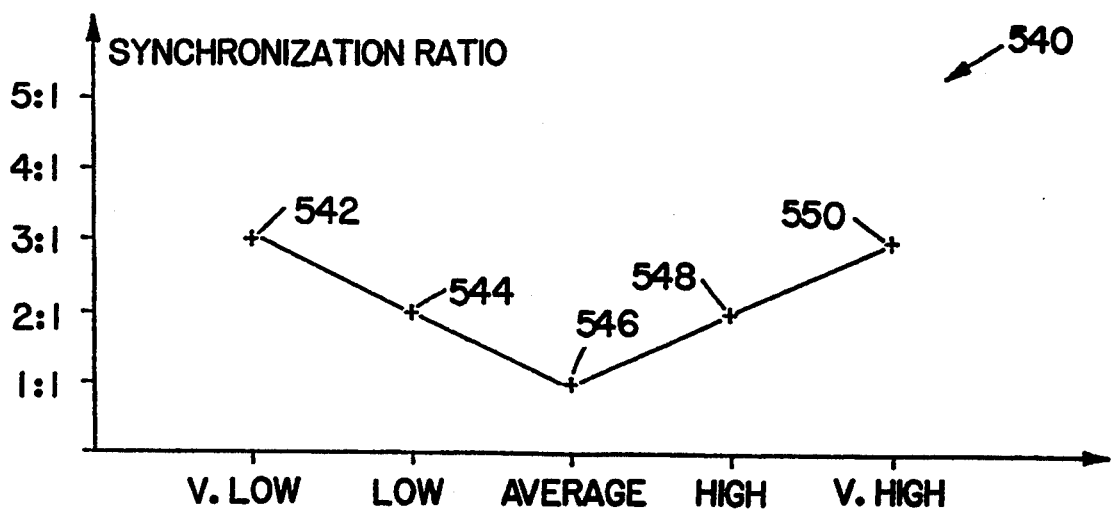
FIG. 16 is a graphical representation of synchronization ratio as a function of activity level.

FIG. 16 is a graphical representation of the synchronization ratio performed by the variable counter of duty cycle timing circuit 764. A one-to-one synchronization ratio is used for average anticipated cardiac demand. This provides the greatest chronic assistance to the myocardium with the least battery consumption by implantable pulse generator 36B. The synchronization ratio is greater for less than average anticipated cardiac demand because less assistance is actually required. The synchronization ratio increases as the anticipated cardiac demand increases to ensure the fatigue of skeletal muscle 22 is minimized.

Figure 17:
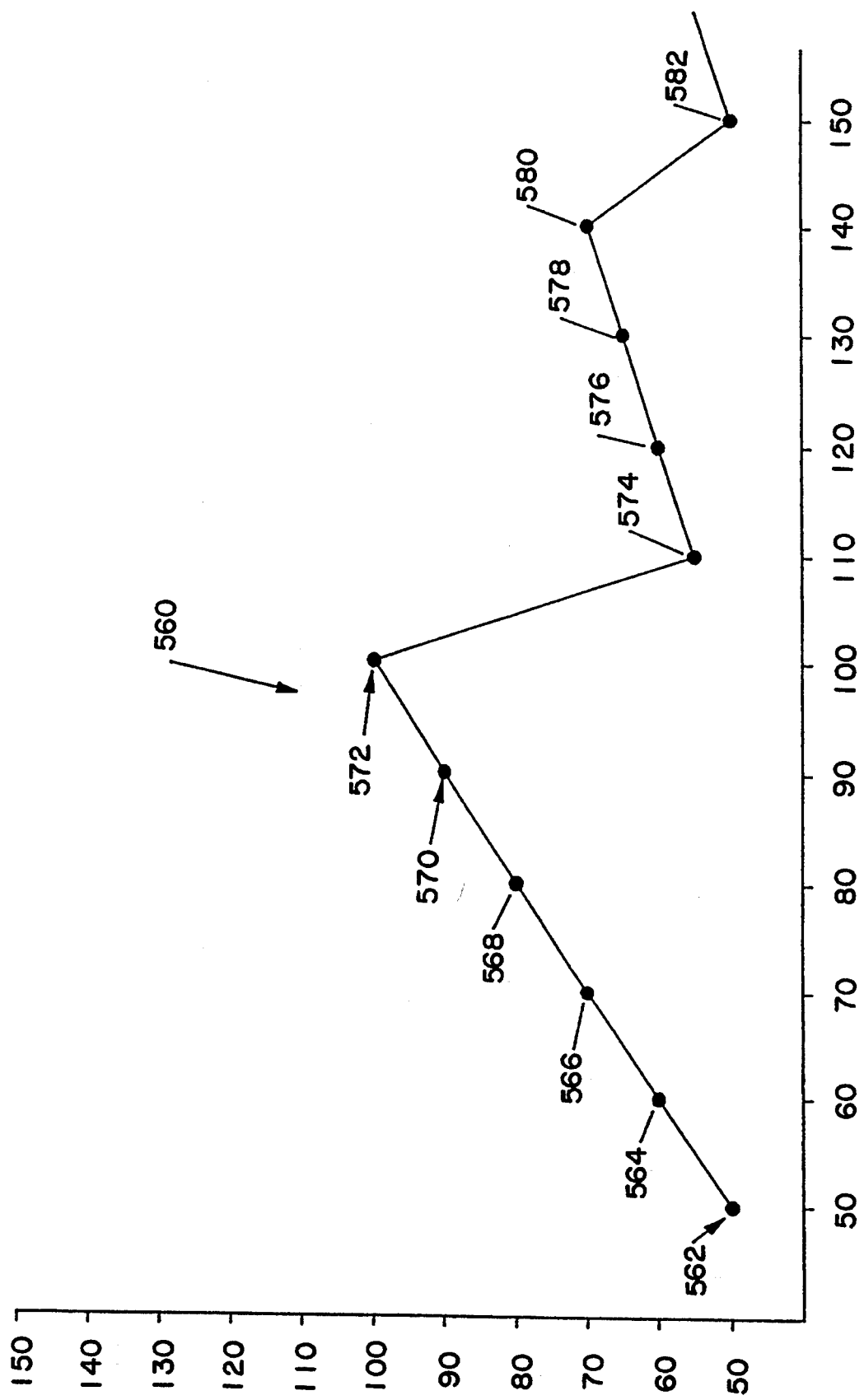
FIG. 17 is a graphical representation of stimulation rate as a function of cardiac rate with decreasing synchronization ratio.

FIG. 17 is a graphical representation of actual cardiac rates on the abscissa in relation to actual rates of stimulation of skeletal muscle 22 along the ordinate. Shown is the change in duty cycle with actual rate. The duty cycle is one-for-one in the typical patient in the range of 50 to 100 beats per minute. At point 572, the actual cardiac rate is 100 beats per minute and the rate of stimulation of skeletal muscle 22 is 100 beats per minute. Above that rate, skeletal muscle 22 is stimulated only once for every two cardiac cycles. At point 580 (140 beats per minute), the duty cycle becomes one stimulation of skeletal muscle 22 for every three cardiac cycles.

Figure 18:
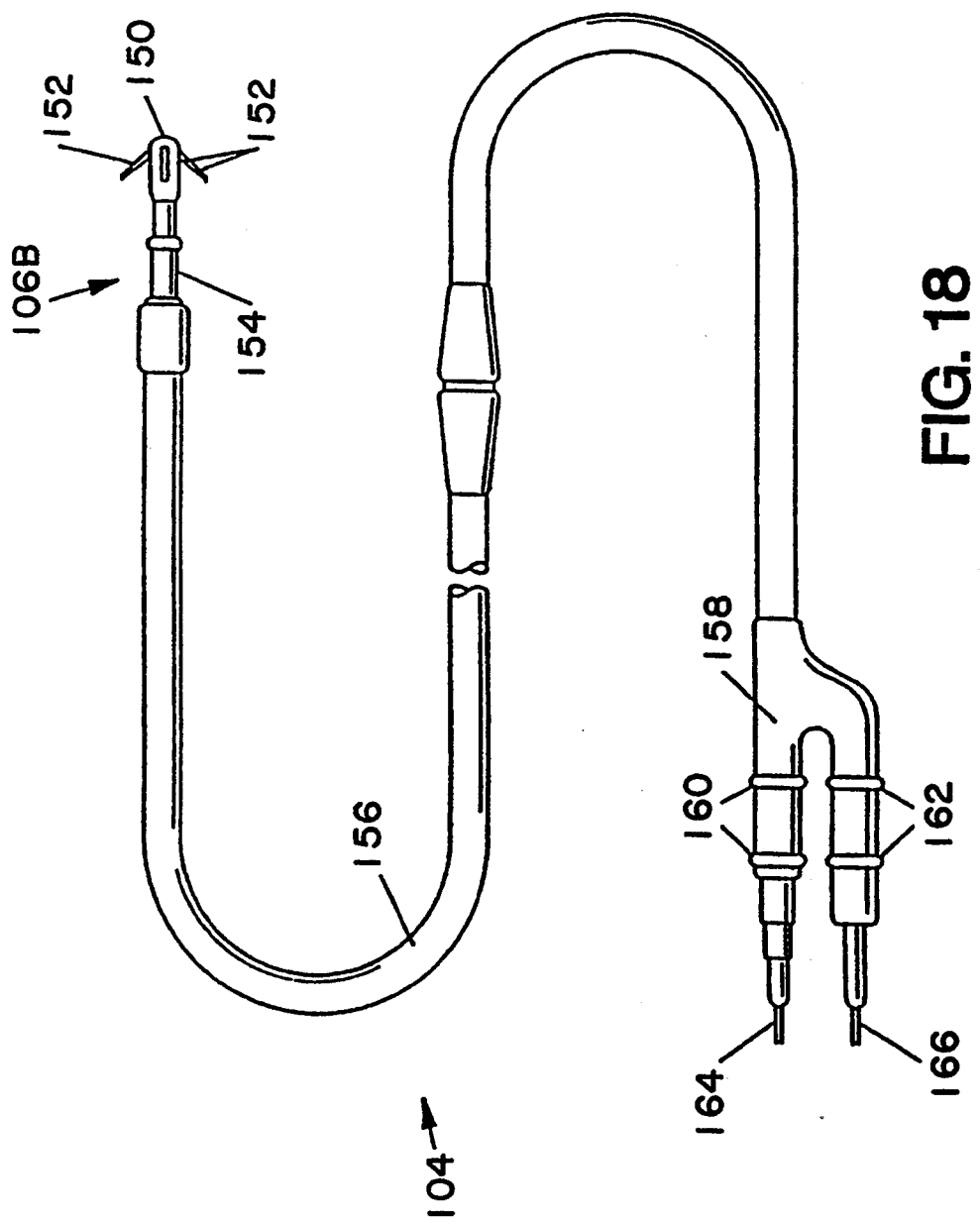
FIG. 18 is a plan view of a sensing lead with temperature sensor attached.

FIG. 18 is a plan view of lead 104 with temperature sensor 106B attached to the distal end. The outer covering of lead 104 is outer sheath 156 which is of a chronically implantable biocompatible material such as medical grade silicone rubber or polyurethane. The proximal end of lead 104 contains bifurcated connector 158 which sealingly inserts into implantable pulse generator 36C. Sealing ring pairs 160 and 162 complete the seal against the ingress of bodily fluids. Lead 104 contains two electrically separated conductors which couple the thermistor of temperature sensor 106B with implantable pulse generator 36C. These two conductors are electrically coupled to terminal pins 164 and 166.

The distal end of lead 104 contains temperature sensor 106B. It is a commonly available thermoresistive device which is housed within rigid housing 154. Preferably rigid housing 154 is a titanium cylinder which is insulated inside and outside with medical grade silicone rubber. The two terminals of the thermistor within rigid housing 154 are coupled to the two conductors within the body of lead 104. The thermistor is thermally coupled to distal tip 150 of temperature sensor 106B which is preferably comprised of a biocompatible material such as titanium. Distal tip 150 is not insulated to promote heat conduction to the thermistor of temperature sensor 106B and therefore must be of a biocompatible material. Tine structures 152 assist in the chronic attachment of temperature sensor 106B within skeletal muscle 22.

Figure 19:
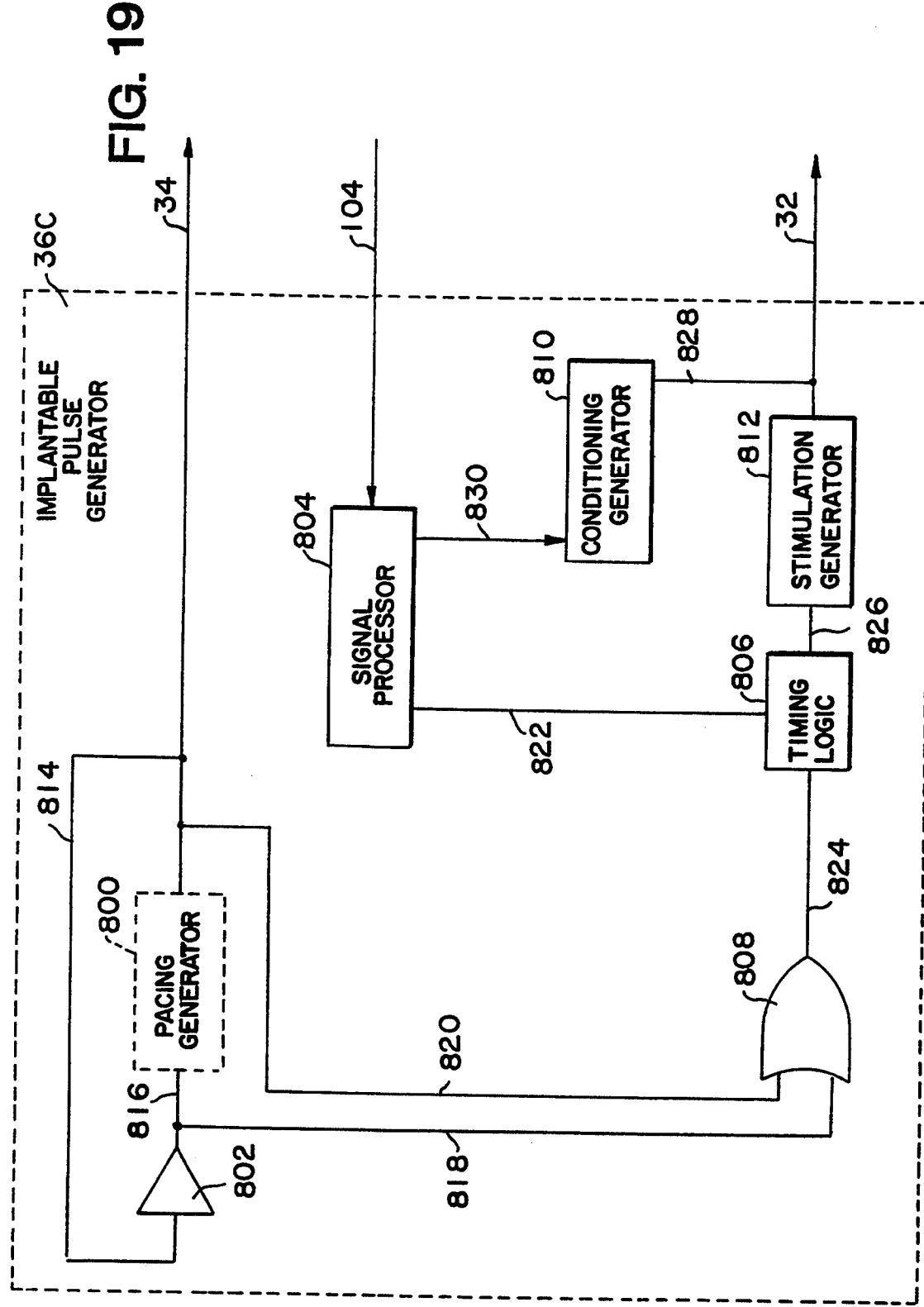
FIG. 19 is a block diagram of an alternative embodiment of the implantable pulse generator.

FIG. 19 is a block diagram of the circuitry of implantable pulse generator 36C, which processes the output of temperature sensor 106B. Pacing lead 34 electrically couples implantable pulse generator 36C to human heart 100 as is shown in FIG. 1. Pacing generator 800 supplies artificial pacing pulses whenever it determines that a naturally occurring pacing event has not transpired at the correct time. Sensing for such a naturally occurring pacing event is facilitated by sense amplifier 802 which is coupled to pacing lead 34 via line 814. The amplified signal is sent to pacing generator 800 by line 816.

The amplified naturally occurring pacing signal is also sent to OR-gate 808 by line 818. OR-gate 808 also receives an indication of an artificial pacing signal via line 820. In either event the output of OR-gate 808 on line 824 indicates the time at which a contraction of human heart 100 has been stimulated, whether naturally or artificially.

Timing logic 806 provides a signal via line 826 to notify stimulation generator 812 to produce a pulse to stimulate contraction of skeletal muscle 22. This signal occurs at a predetermined delay after the contraction of human heart 100. The exact amount of this delay is based upon two factors. The first of these is the configuration of the cardiac assist system. As explained above, this delay is necessary to provide the contraction of skeletal muscle 22 at the proper time relative to human heart 100. This delay is very short for the configuration of FIG. 1 and is quite substantial for the configuration of FIG. 3. The second factor is an adjustment provided by signal processor 804 via line 822. This factor is explained in detail below.

Conditioning generator 810 provides the pulses used to condition skeletal muscle 22 as a "slow twitch" muscle as taught by Cox. These pulses are transferred to skeletal muscle 22 by line 828 and lead 32, along with the stimulation pulses of stimulation generator 812. After skeletal muscle 22 has been fully conditioned as taught by Cox, the conditioning pulses may be replaced by maintenance pulses which differ from conditioning pulses by their lower amplitude and hence lower power requirements. The change to maintenance pulses is triggered by signal processor 804 via line 830 under the conditions as discussed below.

Signal processor 804 is coupled to temperature sensor 106B by the two conductors of lead 104 as explained above. Signal processor 804 uses circuitry known in the art to measure the resistance of the thermistor of temperature sensor 106B, and therefore, the temperature of skeletal muscle 22. Based upon the temperature sensed, signals are sent via lines 822 and 830 to vary the delay of the stimulation pulses and change to maintenance pulses, respectively.

Figure 20:
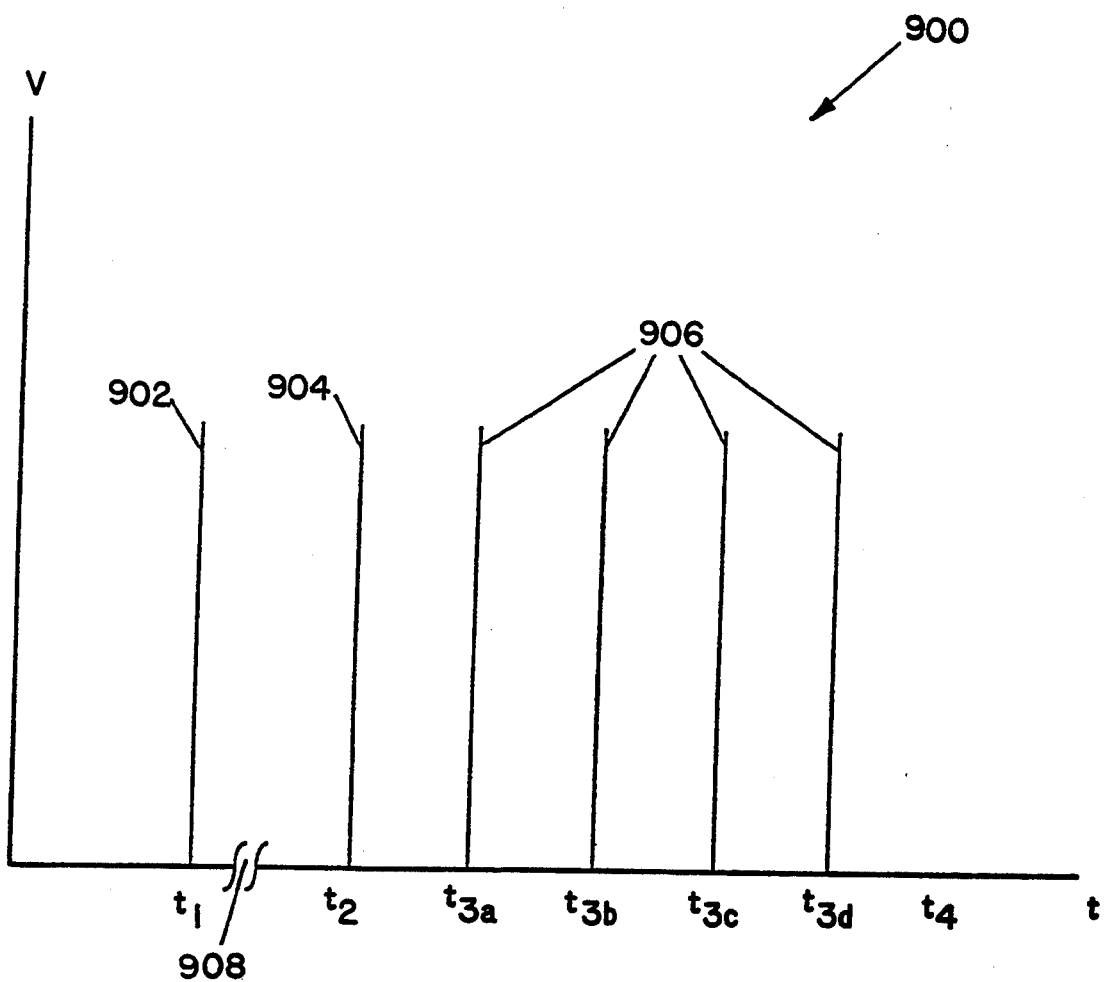
FIG. 20 is a graphical representation of the timing relationship between contractions of the human heart and the pulses produced by the implantable pulse generator.

FIG. 20 is a graphical representation 900 of a single cycle containing a pacing pulse 902 occurring at time t1 and the corresponding pulses transferred to skeletal muscle 22. Stimulation pulse 904 is that pulse which is intended to cause the primary contraction of skeletal muscle 22. It occurs at time t2 following a delay 908. As explained above, delay 908 is a part determined by the configuration of the cardiac assist system and in part by signal processor 804. Following stimulation pulse 904, conditioning/maintenance pulses 906 are generated at times t3a, t3b, t3c, and t3d. These pulses are produced by conditioning generator 810 in accordance with the teaching of Cox.

FIG. 21 is a graphical representation of the force of contraction of skeletal muscle 22 for one unconditioned cycle 918 and one conditioned cycle 910. The force curve for the conditioned cycle 910 is smooth and continuous and is representative of a slow twitch muscle. The force curve for the unconditioned cycle 918 is discontinuous and is characteristic of a fast twitch muscle. Force peaks 912, 914, 916, and 920 are secondary contractions corresponding to the conditioning pulses, occurring at times t3a, t3b, t3c, and t3d, respectively. These specific curves show ideal responses. Actual measurement of these specific curves using a thermistor would probably be very difficult.

Figure 22:
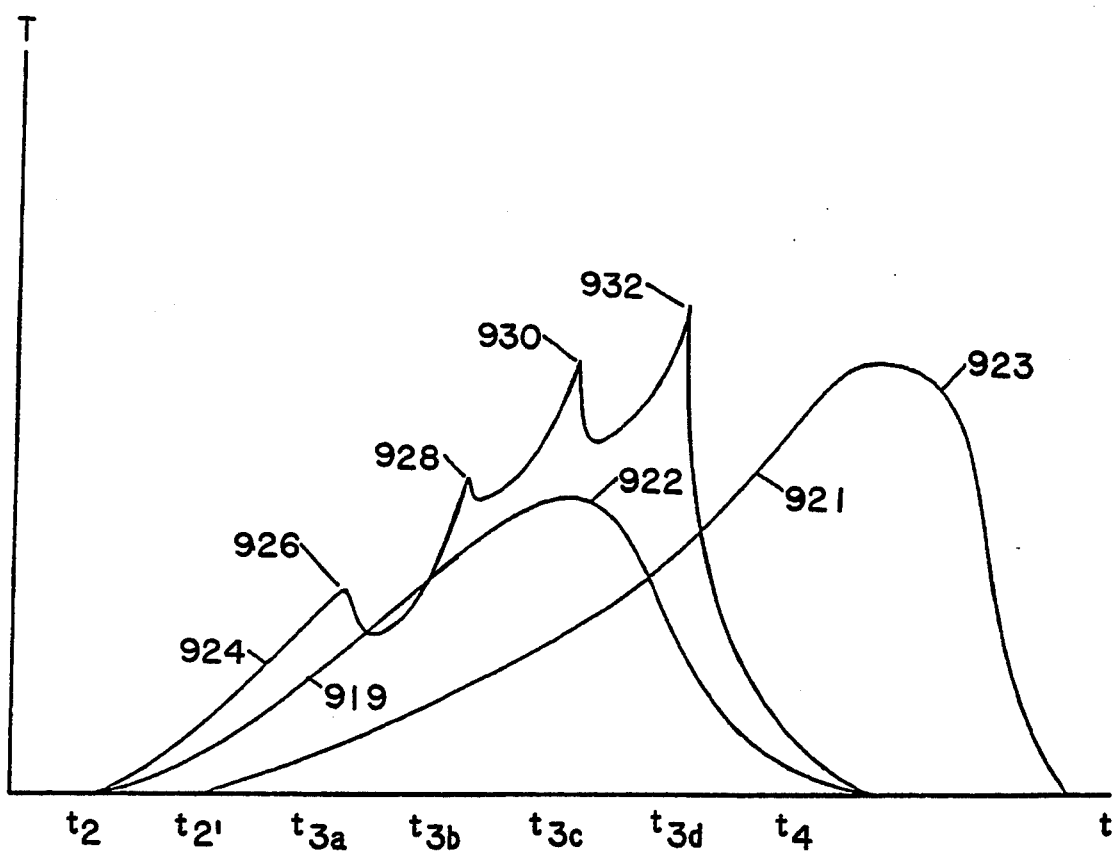
FIG. 22 is a graphical representation of the temperature sensed for unconditioned, conditioned but improperly timed, and conditioned and properly timed skeletal muscle contractions.

FIG. 22 is a graphical representation of the temperature curves measured by temperature sensor 106B under three different situations. Temperature curve 919 corresponds to the ideal situation of a properly timed contraction of a fully conditioned skeletal muscle 22. The two key characteristics of this curve are its smooth and continuous nature and the relatively low peak temperature at peak 922.

Temperature curve 921, on the other hand, although smooth and continuous, is delayed somewhat and reaches a much higher temperature peak 923. This higher temperature peak is readily sensed by signal processor 804 as an improperly timed stimulation pulse. The higher temperature results from the much larger component of isometric and much smaller component of isotonic activity associated with the improperly timed contraction. Upon sensing this elevated temperature peak 923, signal processor 804 notifies timing logic 806 via line 822 to shorten delay 908 (see also FIGS. 19 and 20).

Temperature curve 924 is characteristic of an unconditioned skeletal muscle 22. This temperature curve 924 has a number of relative temperature peaks at 926, 928, 930, and 932. These relative temperature peaks correspond to fast twitch response to the conditioning pulses. Because the skeletal muscle 22 of temperature curve 924 is unconditioned, signal processor 804 must so notify conditioning generator 810 via line 830.

Figure 23:
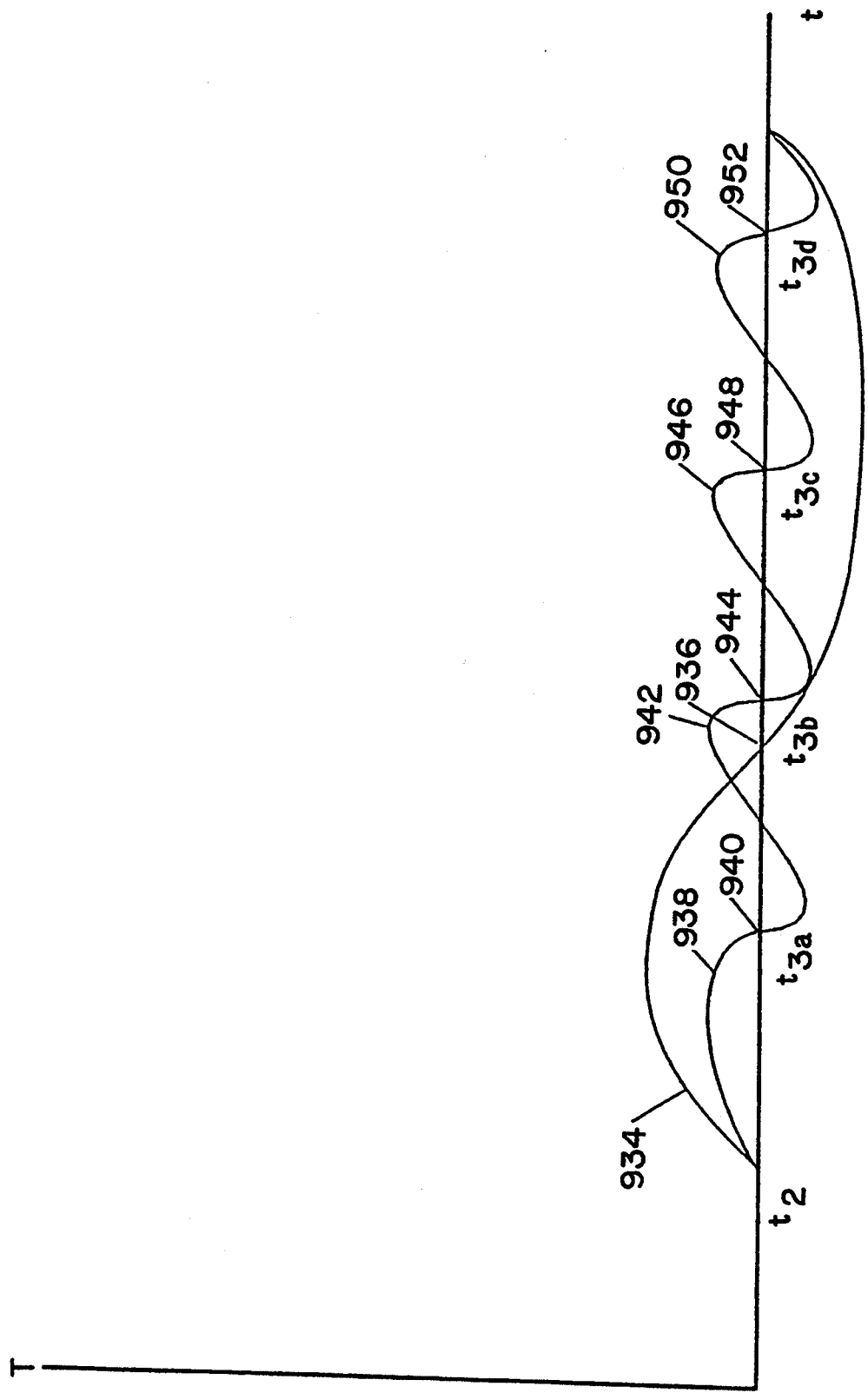
FIG. 23 is a graphical representation of the change in temperature over time for conditioned and unconditioned skeletal muscle.

FIG. 23 is a graphical representation of the differentiated temperature curves 919 and 924 wherein curve 934 corresponds to curve 919 and curve 938 corresponds to curve 924. Through the use of the differentiated temperature curves, signal processor 804 can much more readily distinguish between conditioned and unconditioned skeletal muscle 22. Because curve 934 represents fully conditioned skeletal muscle 22, it has a smooth and continuous temperature curve as explained above, and the corresponding differentiated curve has a single zero crossing at point 936. Differential curve 938, on the other hand, has zero crossings at 940, 944, 948, and 952. This is easily detected by signal processor 804 either digitally or by frequency discrimination using well known techniques.

The foregoing muscle control and monitoring methods and systems can also be used in various applications beyond monitoring skeletal muscles. Exemplary applications include stimulating and training particular muscles to regain control of their deficient functions. For instance, the foregoing methods can be used to stimulate the diaphragms, and the upper and lower limb muscles. Other applications include assisting deficient organs, such in cardiomyoplasty or cardiac assist applications, and neo-sphincter applications where a transferred muscle is stimulated to augment or replace the sphincter function in incontinent patients.

Having thus described the preferred embodiments of the present invention, those of skill in the art will be able to readily apply these teachings to other embodiments without deviating from the scope of the claims hereto attached.

I claim:

1. A cardiac assist system for assisting a natural heart having ventricles which contract at a ventricular rate, said cardiac assist system adapted for coupling to a surgically prepared muscle responsively coupled to said heart and to a circulatory system, and said cardiac assist system comprising:
   a. control means adapted to be coupled to the heart and to the muscle for stimulating the muscle and for causing it to contract in synchrony with said ventricles of said heart; and
   b. means, coupled to said control means and adapted to be responsively coupled to the muscle, for monitoring a parameter indicative of a predetermined level corresponding to adequacy of circulatory support to the muscle.

2. The cardiac assist system according to claim 1 wherein said monitoring means comprises:
   a. means for sensing blood perfusion of the muscle; and
   b. means, responsively coupled to said sensing means, for storing data from said sensing means.

3. The cardiac assist system according to claims 2 further including means for telemetering out the data stored by said storing means.

4. A cardiac assist system according to claim 2 wherein said sensing means is an oximeter.

5. A cardiac assist system according to claim 4 wherein said oximeter is a two wavelength reflectance oximeter.

6. The cardiac assist system according to claim 4 further including means for telemetering out the data stored by said storing means.

7. The cardiac assist system according claim 1, wherein said monitoring means includes means for sensing a level of oxygen in the muscle.

8. An assist system for assisting an organ, said assist system adapted for coupling to a surgically prepared muscle responsively coupled to said organ and to a circulatory system- has been inserted after "muscle". the assist system comprising:
   a. control means adapted to be coupled to the organ and to the muscle for stimulating the muscle and for causing it to contract in a predetermined sequence; and
   b. means, coupled to said control means and adapted to be responsively coupled to the muscle, for monitoring a parameter indicative of a predetermined level corresponding to adequacy of circulatory support to the muscle.

* * * * *